(12) United States Patent
Torrie et al.

(10) Patent No.: US 7,153,312 B1
(45) Date of Patent: Dec. 26, 2006

(54) CLOSURE DEVICE AND METHOD FOR TISSUE REPAIR

(75) Inventors: Paul A. Torrie, Marblehead, MA (US); George Sikora, Mansfield, MA (US); Raymond A. Bojarski, Attleboro, MA (US)

(73) Assignee: Smith & Nephew Inc., Memphis, TN (US)

( * ) Notice: Subject to any disclaimer, the term of this patent is extended or adjusted under 35 U.S.C. 154(b) by 772 days.

(21) Appl. No.: 09/704,926

(22) Filed: Nov. 2, 2000

Related U.S. Application Data

(63) Continuation-in-part of application No. 09/453,120, filed on Dec. 2, 1999, now abandoned.

(51) Int. Cl.
*A61B 17/04* (2006.01)

(52) U.S. Cl. ...................................................... 606/144
(58) Field of Classification Search ................. 606/139, 606/144, 145, 148
See application file for complete search history.

(56) References Cited

U.S. PATENT DOCUMENTS

| 233,475 | A | 10/1880 | Cook et al. |
|---|---|---|---|
| 261,501 | A | 7/1882 | Vandermark |
| 1,635,066 | A | 7/1927 | Wells |
| 2,610,631 | A | 9/1952 | Calicchio |
| 2,880,728 | A | 4/1959 | Rights |
| 2,881,762 | A | 4/1959 | Lowrie |

(Continued)

FOREIGN PATENT DOCUMENTS

| EP | 0108912 | 5/1984 |
|---|---|---|
| EP | 0 260 970 A2 | 3/1988 |
| EP | 0315371 | 5/1989 |
| EP | 0598219 | 5/1994 |
| EP | 0 913 123 A1 | 5/1999 |
| EP | 1 013 229 A2 | 6/2000 |
| WO | 98/22047 | 5/1998 |
| WO | 99/01084 | 1/1999 |
| WO | WO 99/12480 | 3/1999 |
| WO | WO 01/39671 A1 | 6/2001 |

OTHER PUBLICATIONS

Sotereanos, D. G. "Rotator Cuff Repair Using PANALOK RC Absorbable Anchor," undated.

Thal, R. "A Knotless Suture Anchor & Method for Arthroscopic Bankart Repair Introduction," Poster Board No.: 296 at the 1999 Annual Meeting of the American Academy of Orthopaedic Surgeons.

Thal, R. "A Knotless Suture Anchor: Technique for Use in Arthroscopic Bankart Repair," undated.

*Primary Examiner*—John J. Calvert
*Assistant Examiner*—Shaun R Hurley
(74) *Attorney, Agent, or Firm*—Fish & Richardson P.C.

(57) ABSTRACT

A surgical method includes positioning a fixation member relative to tissue, moving a flexible member coupled to the fixation member relative to the fixation member to bring two tissue surfaces together, and moving a retaining element coupled to the flexible member relative to the fixation member. The retaining element acts to limit loosening of the flexible member relative to the fixation member. An apparatus for repairing a tear in soft tissue includes first and second fixation members, a flexible member substantially immovably secured to the first fixation member and movably coupled to the second fixation member, and a retaining element coupled to the flexible member. In another embodiment, an apparatus for repairing a tear in soft tissue includes a fixation member, and a flexible member movably coupled to the fixation member. A first end of the flexible member is looped back and secured to the flexible member.

61 Claims, 28 Drawing Sheets

U.S. PATENT DOCUMENTS

| | | |
|---|---|---|
| 3,618,447 A | 11/1971 | Goins |
| 3,664,345 A | 5/1972 | Dabbs et al. |
| 3,716,058 A | 2/1973 | Tanner, Jr. |
| 3,752,516 A | 8/1973 | Mumma |
| 3,757,629 A | 9/1973 | Schneider |
| 3,825,010 A | 7/1974 | McDonald |
| 3,840,017 A | 10/1974 | Violante |
| 3,842,824 A | 10/1974 | Neufeld |
| 3,842,840 A | 10/1974 | Schweizer |
| 3,867,944 A | 2/1975 | Samuels |
| 3,871,379 A | 3/1975 | Clarke |
| 3,910,281 A | 10/1975 | Kletschka et al. |
| 3,946,740 A | 3/1976 | Bassett |
| 3,976,079 A | 8/1976 | Samuels et al. |
| 3,985,138 A | 10/1976 | Jarvik |
| 4,006,747 A | 2/1977 | Kronenthal et al. |
| 4,235,238 A | 11/1980 | Ogiu et al. |
| 4,326,531 A | 4/1982 | Shimonaka |
| 4,493,323 A | 1/1985 | Albright et al. |
| 4,505,274 A | 3/1985 | Speelman |
| 4,531,522 A | 7/1985 | Bedi et al. |
| 4,534,350 A | 8/1985 | Golden et al. |
| 4,570,623 A | 2/1986 | Ellison et al. |
| 4,595,007 A | 6/1986 | Mericle |
| 4,596,249 A | 6/1986 | Freda et al. |
| 4,602,635 A | 7/1986 | Mulhollan et al. |
| 4,616,650 A | 10/1986 | Green et al. |
| 4,624,254 A | 11/1986 | McGarry et al. |
| 4,635,637 A | 1/1987 | Schreiber |
| 4,636,121 A | 1/1987 | Miller |
| 4,641,652 A | 2/1987 | Hutterer et al. |
| 4,662,068 A | 5/1987 | Polonsky |
| 4,705,040 A | 11/1987 | Mueller et al. |
| 4,719,917 A | 1/1988 | Barrows et al. |
| 4,723,540 A | 2/1988 | Gilmer, Jr. |
| 4,724,839 A | 2/1988 | Bedi et al. |
| 4,741,330 A | 5/1988 | Hayhurst |
| 4,741,336 A | 5/1988 | Failla et al. |
| 4,750,492 A | 6/1988 | Jacobs |
| 4,781,190 A | 11/1988 | Lee |
| 4,809,695 A | 3/1989 | Gwathmey et al. |
| 4,823,794 A | 4/1989 | Pierce |
| 4,841,960 A | 6/1989 | Garner |
| 4,858,608 A | 8/1989 | McQuilkin |
| 4,873,976 A | 10/1989 | Schreiber |
| 4,887,601 A | 12/1989 | Richards |
| 4,890,615 A | 1/1990 | Caspari et al. |
| 4,895,148 A | 1/1990 | Bays et al. |
| 4,923,461 A | 5/1990 | Caspari et al. |
| 4,950,285 A | 8/1990 | Wilk |
| 4,961,741 A | 10/1990 | Hayhurst |
| 4,983,176 A | 1/1991 | Cushman et al. |
| 5,041,129 A | 8/1991 | Hayhurst et al. |
| 5,053,047 A | 10/1991 | Yoon |
| 5,059,201 A | 10/1991 | Asnis |
| 5,084,050 A | 1/1992 | Draenert |
| 5,084,058 A | 1/1992 | Li |
| 5,087,263 A | 2/1992 | Li |
| 5,123,913 A | 6/1992 | Wilk et al. |
| 5,149,329 A | 9/1992 | Richardson |
| 5,154,189 A | 10/1992 | Oberlander |
| 5,178,629 A | 1/1993 | Kammerer |
| 5,211,650 A | 5/1993 | Noda |
| 5,258,015 A | 11/1993 | Li et al. |
| 5,269,809 A | 12/1993 | Hayhurst et al. |
| 5,282,809 A | 2/1994 | Kammerer et al. |
| 5,318,577 A | 6/1994 | Li |
| 5,336,229 A | 8/1994 | Noda |
| 5,336,231 A | 8/1994 | Adair |
| 5,342,369 A | 8/1994 | Harryman, II |
| 5,417,691 A | 5/1995 | Hayhurst |
| 5,439,684 A | 8/1995 | Prewett et al. |
| 5,447,512 A | 9/1995 | Wilson et al. |
| 5,467,786 A | 11/1995 | Allen et al. |
| 5,474,572 A | 12/1995 | Hayhurst |
| 5,490,750 A | 2/1996 | Gundy |
| 5,496,331 A | 3/1996 | Xu et al. |
| 5,522,820 A | 6/1996 | Caspari et al. |
| 5,573,286 A | 11/1996 | Rogozinski |
| 5,641,256 A | 6/1997 | Gundy |
| 5,658,299 A | 8/1997 | Hart |
| 5,690,678 A | 11/1997 | Johnson |
| 5,702,462 A | 12/1997 | Oberlander |
| 5,713,904 A | 2/1998 | Errico et al. |
| 5,716,359 A | 2/1998 | Ojima et al. |
| 5,720,765 A | 2/1998 | Thal |
| 5,728,109 A | 3/1998 | Schulze et al. |
| 5,728,136 A | 3/1998 | Thal |
| 5,746,754 A | 5/1998 | Chan |
| 5,749,898 A | 5/1998 | Schulze et al. |
| 5,782,864 A | 7/1998 | Lizardi |
| 5,797,928 A * | 8/1998 | Kogasaka .................. 606/144 |
| 5,810,848 A * | 9/1998 | Hayhurst .................... 606/144 |
| 5,814,069 A | 9/1998 | Schulze et al. |
| 5,843,084 A | 12/1998 | Hart et al. |
| 5,846,254 A | 12/1998 | Schulze et al. |
| 5,871,490 A | 2/1999 | Schulze et al. |
| 5,891,168 A | 4/1999 | Thal |
| 5,893,592 A | 4/1999 | Schulze et al. |
| 5,895,395 A | 4/1999 | Yeung |
| 5,897,564 A | 4/1999 | Schulze et al. |
| 5,954,747 A | 9/1999 | Clark |
| 5,976,127 A | 11/1999 | Lax |
| 5,980,524 A | 11/1999 | Justin et al. |
| 6,024,758 A | 2/2000 | Thal |
| 6,045,574 A | 4/2000 | Thal |
| 6,117,160 A | 9/2000 | Bonutti |
| 6,143,017 A | 11/2000 | Thal |
| 6,152,934 A * | 11/2000 | Harper et al. ............... 606/139 |
| 6,152,936 A * | 11/2000 | Christy et al. .............. 606/148 |
| 6,156,039 A | 12/2000 | Thal |
| 6,306,159 B1 | 10/2001 | Schwartz et al. |
| 6,319,271 B1 | 11/2001 | Schwartz et al. |

* cited by examiner

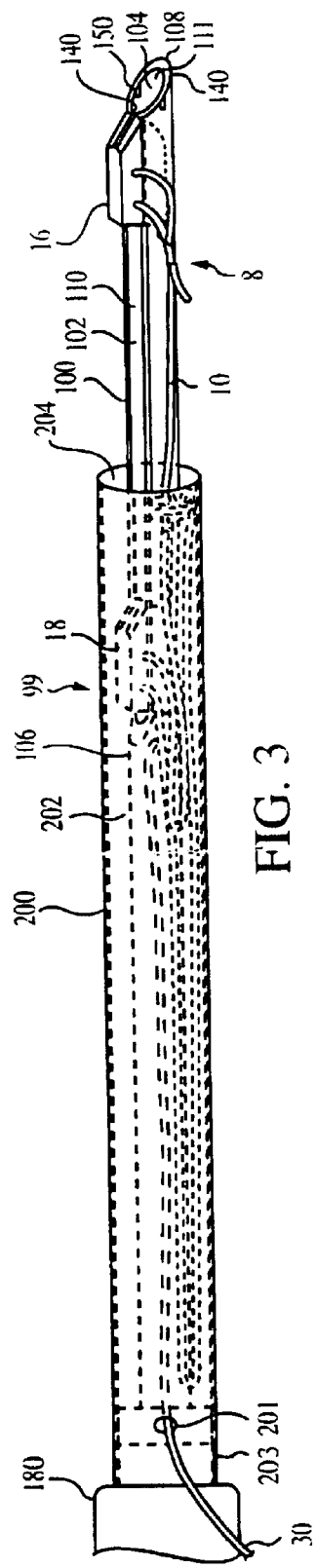
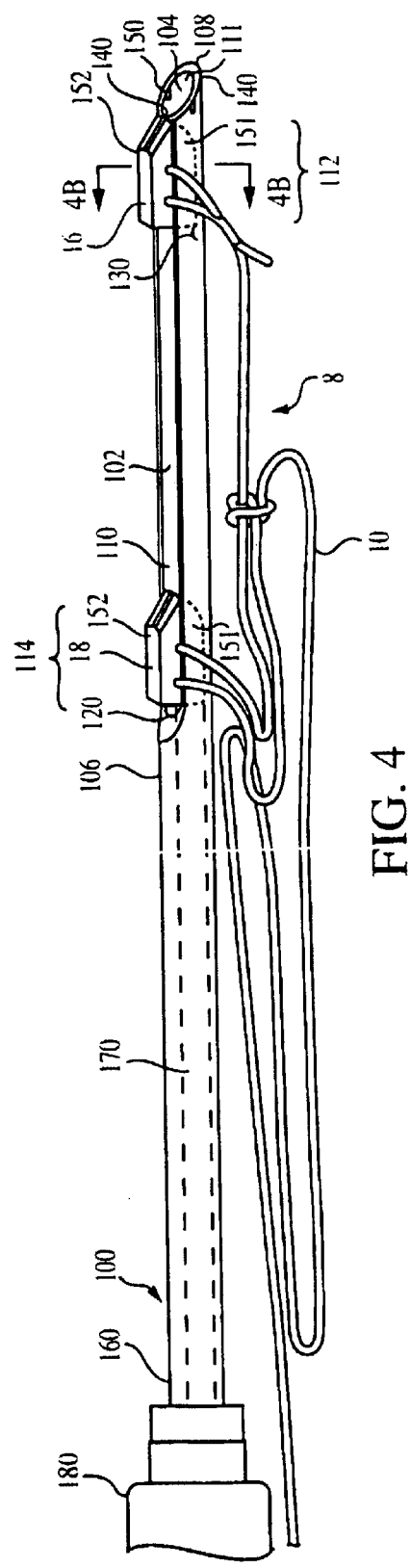

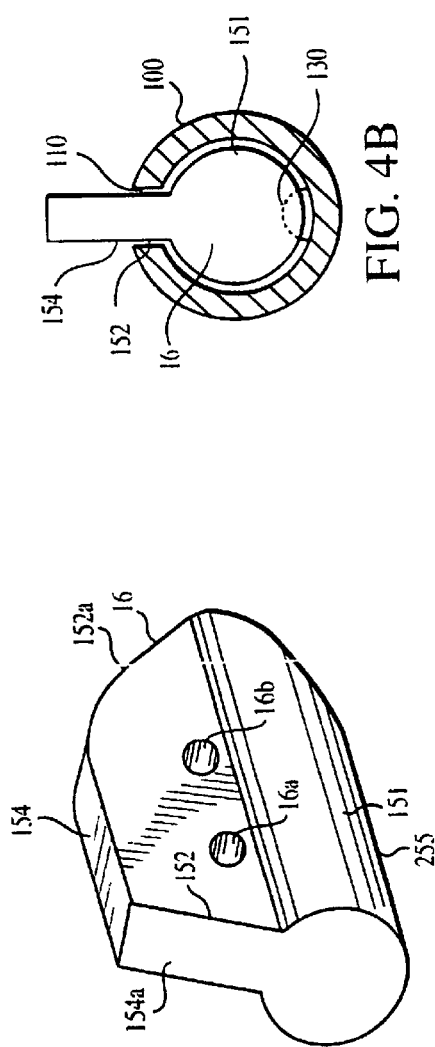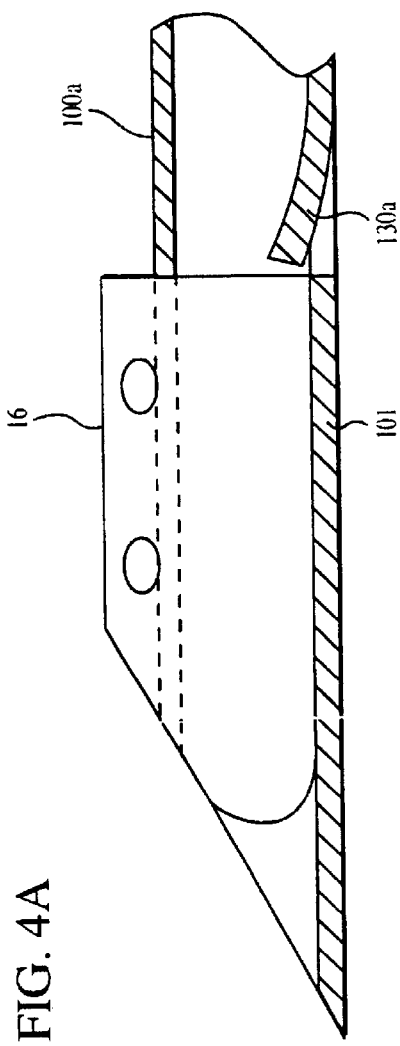
FIG. 4B
FIG. 4C
FIG. 4A

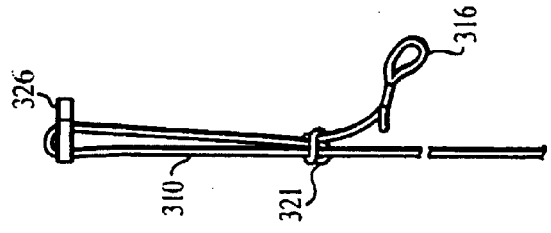
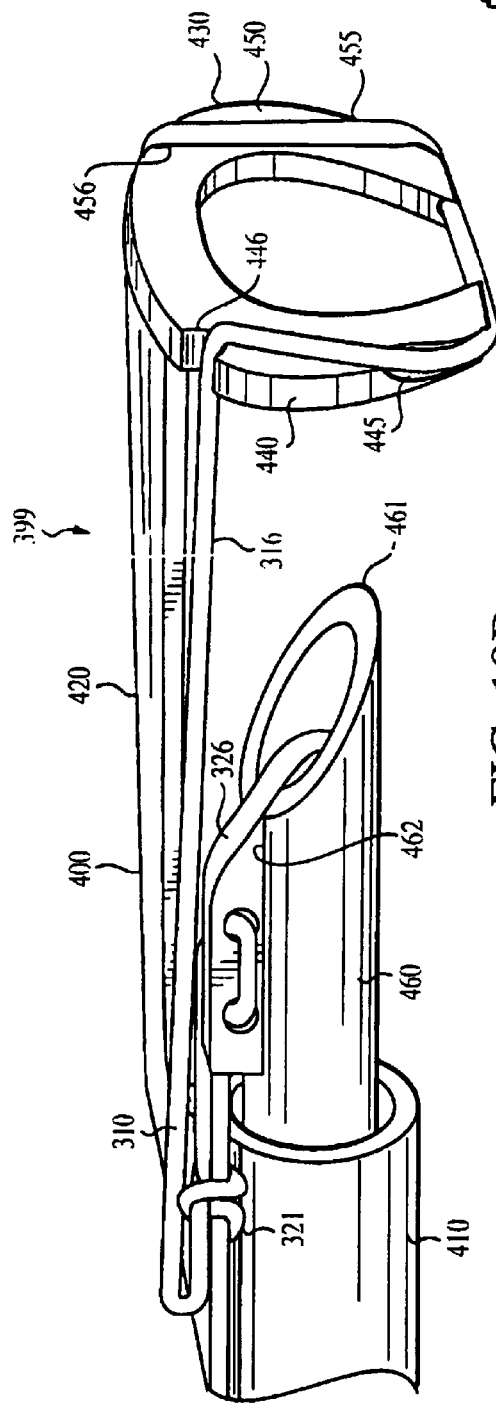

CLOSURE DEVICE AND METHOD FOR TISSUE REPAIR

This application is a continuation-in-part of U.S. Ser. No. 09/453,120, filed Dec. 2, 1999, entitled WOUND CLOSURE DEVICES AND METHODS, now abandoned and hereby incorporated herein by reference in its entirety.

BACKGROUND

The invention relates to a closure device and method for tissue repair.

Fibrous tissue wounds, such as muscle, ligament, and cartilage tears, can be repaired arthroscopically using sutures. Traditionally, to close a fibrous tissue wound, a surgeon would insert two suture needles into the tissue with sutures attached, thread the sutures across the wound, and then tie knots to fix the free ends of the sutures within the tissue.

To simplify the wound closure procedure and to improve fixation, various types of suture anchors have been developed. One example of a suture anchor is disclosed in Hayhurst, U.S. Pat. No. 4,741,330, which is incorporated herein by reference. In Hayhurst, one end of a suture is fixed to a resiliently-deformable, bar-shaped suture anchor. The anchor is loaded into the bore of a hollow needle and deployed into or against the fibrous tissue. The surgeon then threads the suture across the wound and tensions a free end of the suture to pull the wound closed. When the surgeon tensions the suture, the bar in the anchor becomes oriented transversely to the suture hole, anchoring the suture in place.

SUMMARY

According to one aspect of the invention, a surgical method includes positioning a fixation member relative to tissue, moving a flexible member coupled to the fixation member relative to the fixation member to bring two tissue surfaces together, and moving a retaining element coupled to the flexible member relative to the fixation member. The retaining element acts to limit loosening of the flexible member relative to the fixation member.

Embodiments of this aspect of the invention may include one or more of the following features.

The step of moving the flexible member comprises pulling the flexible member. The step of moving the flexible member also accomplishes the step of moving the retaining element, which is, for example, a slip knot. Alternatively, the step of moving the retaining element includes moving the retaining element relative to the flexible element. The retaining element is, for example, a friction element which permits sliding of the retaining element relative to the flexible element in only one direction. In another illustrated embodiment the retaining element is in the form of an overhand knot, and the method includes advancing the overhand knot along the flexible element. In another illustrated embodiment, the retaining element is in the form of a Chinese trap.

In an exemplary embodiment, the step of moving the flexible member includes pulling on only one end of the flexible member.

In another illustrated embodiment, the method includes positioning a second fixation member relative to the tissue. The second fixation member is coupled to the flexible member, either movably or fixedly. The step of moving the flexible member includes, for example, pulling on two ends of the flexible member or pulling on only one end of the flexible member.

The step of positioning the fixation member includes positioning the fixation member on an outer surface of the tissue, and the two tissue surfaces brought together are both soft tissue. Alternatively, the fixation member is positioned in a bone hole, and one of the two tissue surfaces brought together is bone and the other soft tissue.

In another illustrated embodiment, the step of positioning the fixation member includes passing the fixation member through a loop of the flexible member. The loop is positioned within a tear in soft tissue.

According to another aspect of the invention, a method for repairing a tear in soft tissue includes advancing a fixation member coupled to a flexible member through tissue on either side of the tear and through a loop of the flexible member, and tensioning the flexible member to bring two tissue surfaces on either side of the tear together.

Embodiments of this aspect of the invention may include one or more of the following features. The loop is positioned within the tear. The method includes pulling an end of the flexible member to bring the two tissue surfaces together. The fixation member is in the form of a barbed member.

According to another aspect of the invention, an apparatus for repairing a tear in soft tissue includes at least two fixation members, a flexible member substantially immovably secured to the first fixation member and movably coupled to the second fixation member, and a retaining element coupled to the flexible member. The retaining element is movable relative to the second fixation member and acts to limit loosening of the flexible member relative to the fixation member.

According to another aspect of the invention, an apparatus for repairing a tear in soft tissue includes at least two fixation members, a flexible member substantially immovably secured to the first fixation member and movably coupled to the second fixation member, and a retaining element coupled to the flexible member. The retaining element is slidably received by the flexible member and acts to limit loosening of the flexible member relative to the fixation member.

According to another aspect of the invention, an apparatus for repairing a tear in soft tissue includes a fixation member, and a flexible member movably coupled to the fixation member. A first end of the flexible member is looped back and secured to the flexible member to form a loop. The loop is remote from the fixation member.

According to another aspect of the invention, a flexible member holder includes a shaft, a first tine at an end region of the shaft defining a first region for receiving a first portion of a loop of a flexible member, and a second tine at the end region of the shaft defining a second region for receiving a second portion of the loop of the flexible member.

Embodiments of this aspect of the invention may include one or more of the following features. The shaft is a tube. The first and second regions are grooves.

According to another aspect of the invention, a device for repairing a tear in a tissue includes a needle having a distal region defined between two holding elements, and a proximal region. A first fixation member is positioned within the distal region and a second fixation member is positioned within the proximal region. A flexible member is coupled to the first and second fixation members.

Embodiments of this aspect of the invention may include one or more of the following features. A first of the holding elements is a crimp in the needle in the distal region, and the second holding element is a dimple or ramp extending into a lumen of the needle. The needle wall has a slot and the fixation members extend through the slot. The needle is sized to fit into an end of a protector tube. A push pin is sized to fit inside the needle.

Embodiments of the invention may include one or more of the following advantages. The length of a flexible member spanning across a tear in tissue can be shortened to close the tear by tensioning the flexible member with no additional manipulation being required to limit loosening of the flexible member. First and second fixation members can be deployed using a single hollow needle, rather than two separate needles. After deploying a fixation member, the surgeon need not tie an additional knot. The length of a flexible member coupled to the fixation member can be adjusted after deploying the fixation member, allowing a surgeon to set the tension in the flexible member to a desired level.

Since the device uses a flexible member, such as a suture, to close the tissue wound, rather than inflexible staples or tacks, the tissue is not significantly damaged when it expands and contracts. For example, if the soft tissue is a meniscus, the fixation members do not damage the meniscal tissue when the knee moves.

The details of one or more embodiments of the invention are set forth in the accompanying drawings and the description below. Other features, objects, and advantages of the invention will be apparent form the description and drawings, and from the claims.

DESCRIPTIONS OF DRAWINGS

FIG. 3 is a perspective view of a delivery device for inserting the closure device of FIG. 1 into soft tissue;

FIG. 4 is a perspective view of the delivery device of FIG. 3 shown with an outer sheath removed;

FIG. 4A is a perspective view of a fixation member of the closure device of FIG. 1;

FIG. 4B is a cross-sectional end view of the delivery device of FIG. 4, taken along lines 4B—4B;

FIG. 4C is a cross-sectional side view of an alternative embodiment of a needle of the delivery device of FIG. 3.

FIG. 19B is a perspective view similar to that of FIG. 19A shown with the closure device of FIG. 16;

FIG. 19C is an illustration of the closure device of FIG. 16;

DETAILED DESCRIPTION

Figure 1:
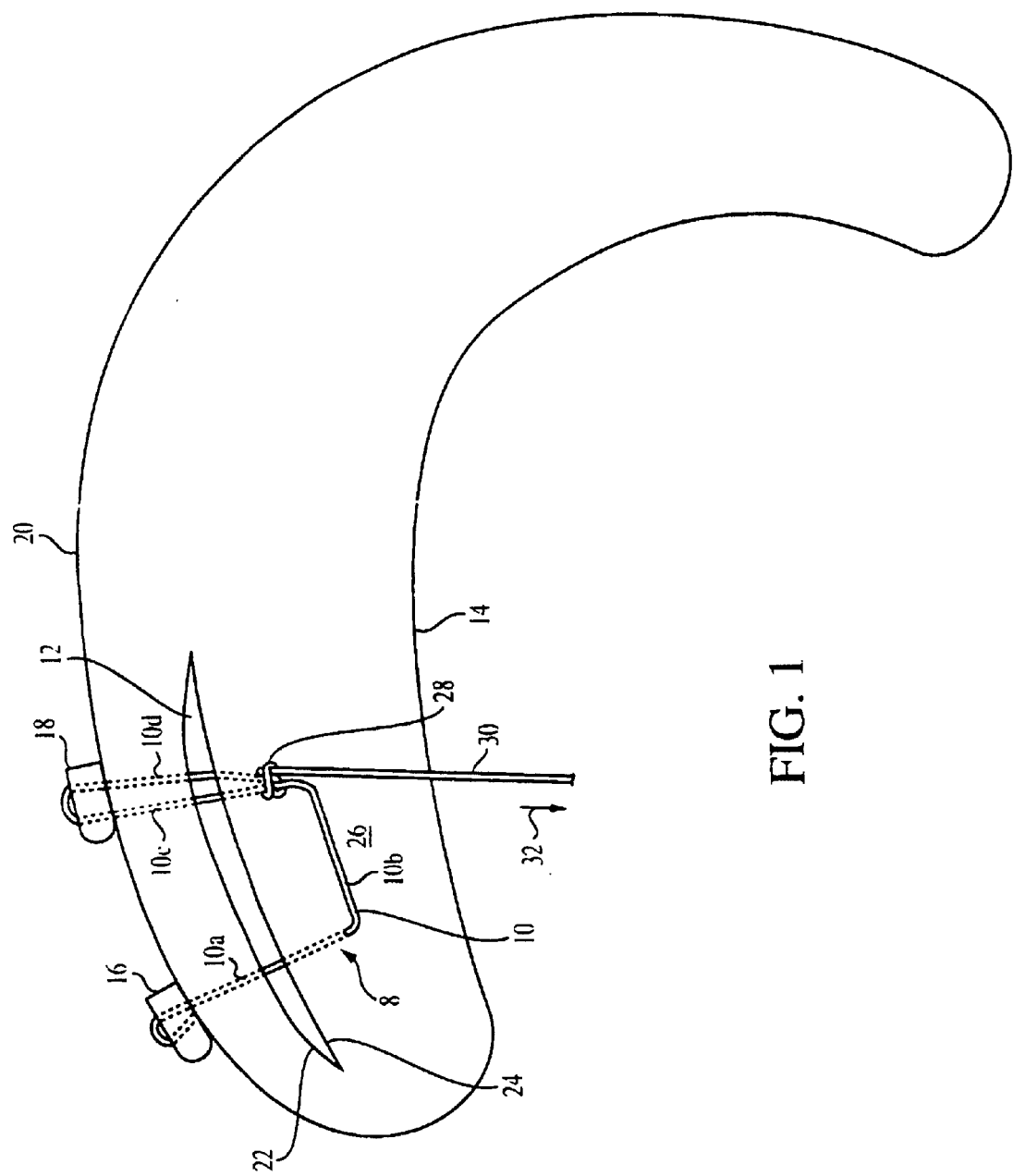
FIG. 1 is an illustration of a closure device according to the invention, shown mending a tear in soft tissue.

Referring to FIG. 1, a closure device 8 for mending a tear 12 in soft tissue 14, e.g., meniscus of the knee joint, includes a flexible member, e.g., suture 10, coupled to a first fixation member 16 and a second fixation member 18. Suture 10 is fastened to fixation member 16 to limit movement of suture 10 relative to fixation member 16, while suture 10 is movable relative to fixation member 18.

Figure 10:
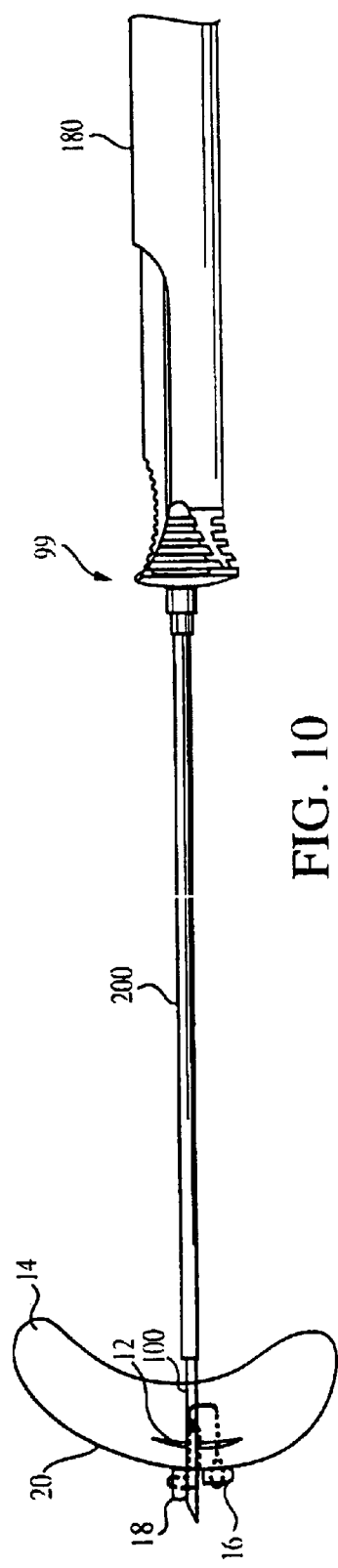

When implanted in the knee joint, fixation members 16 and 18 lie on a surface 20 of tissue 14, for example, the outer surface of the meniscus. Suture 10 has a first suture length 10a extending from first fixation member 16 through tissue 14, traversing tear 12, and emerging at a surface 26 of tissue 14; a second suture length 10b extending across surface 26; a third suture length 10c extending back through tissue 14, traversing tear 12 at a location spaced from first length 10a, and emerging at tissue surface 20 where suture 10 loops through second fixation member 18; and a fourth suture length 10d extending from second fixation member 18 through tissue 14, traversing tear 12, and emerging at surface 26. Suture 10 has a free end 30 which the surgeon pulls, in the direction of arrow 32, to bring sides 22, 24 of tear 12 together into juxtaposition (as shown in FIG. 10).

As described further below, suture portion 10c and suture portion 10d are tied together prior to implantation of device 8 to form a retaining element in the form of a slip knot 28 that allows suture 10 to be pulled in the direction of arrow 32, but does not allow tension on suture 10 to pull suture 10 in the opposite direction, which would allow tear 12 to re-open.

Figure 2A:
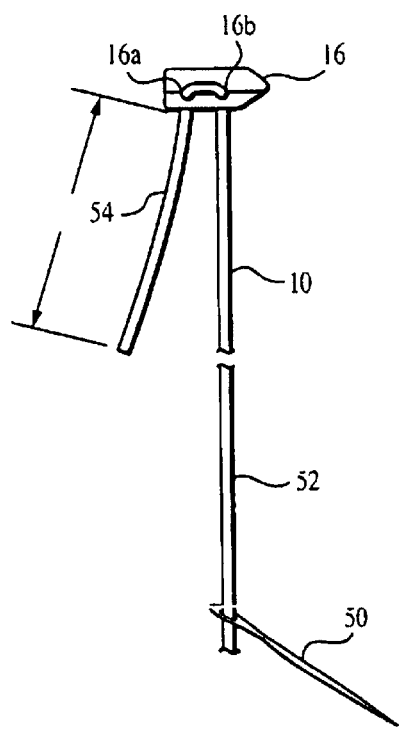
FIGS. 2A–2I show a method of typing a slip knot in suture of the closure device of FIG. 1.
Figure 2B:
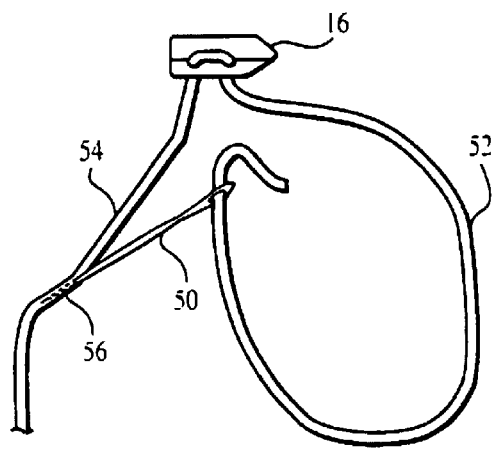
Figure 2C:
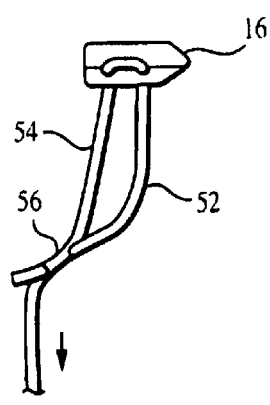
Figure 2D:
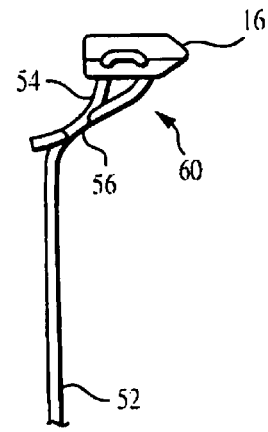

Referring to FIGS. 2A–2I, prior to insertion into tissue 14, suture 10 is attached to fixation members 16, 18 and slip knot 28 is formed. Fixation member 16 defines holes 16*a*, 16*b* for receiving suture 10, and fixation member 18 defines holes 18*a*, 18*b* for receiving suture 10. As illustrated in FIGS. 2A–2D, suture 10 is attached to fixation member 16 by threading suture 10 through a needle 50, and passing needle 50 and suture 10 through holes 16*a*, 16*b* in fixation member 16 (FIG. 2A). Suture 10 now defines a long suture section 52 and a short suture section 54. Long suture section 52 is then attached to short suture section 54 by passing needle 50 and long suture section 52 through short suture section 54 at a region 56 (FIG. 2B). Pulling long suture section 52 away from fixation member 16 (FIG. 2C) then draws region 56 toward fixation member 16 forming a knot 60 (FIG. 2D). Suture 10 is now secured to fixation member 16.

Figure 2E:
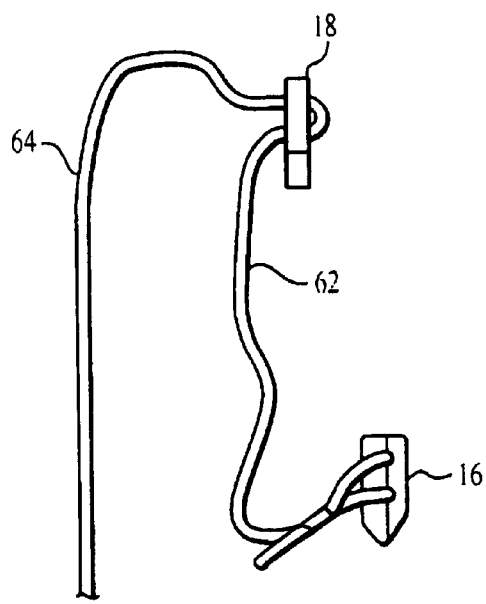
Figure 2F:
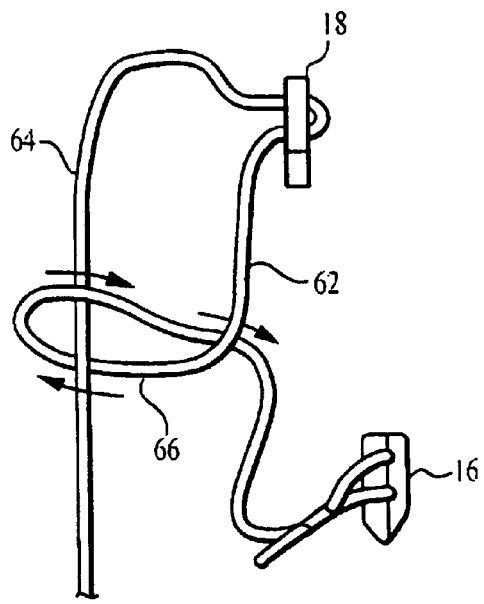
Figure 2G:
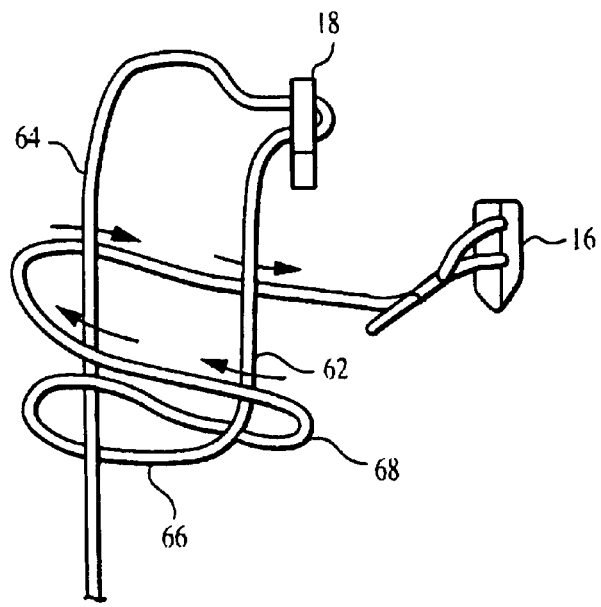
Figure 2H:
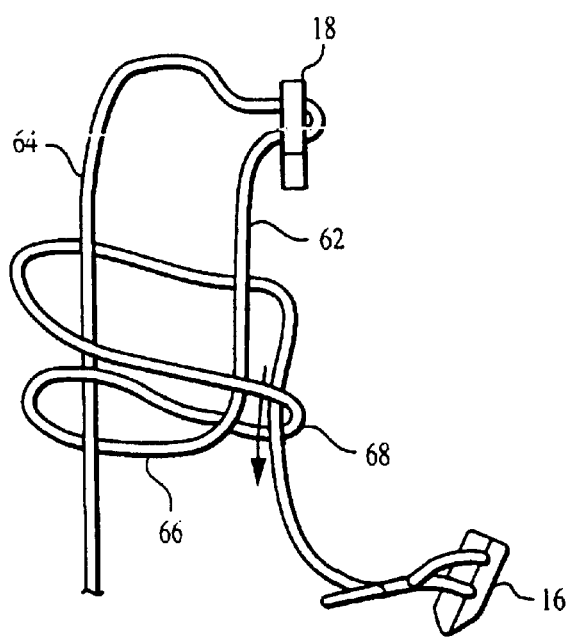
Figure 2I:
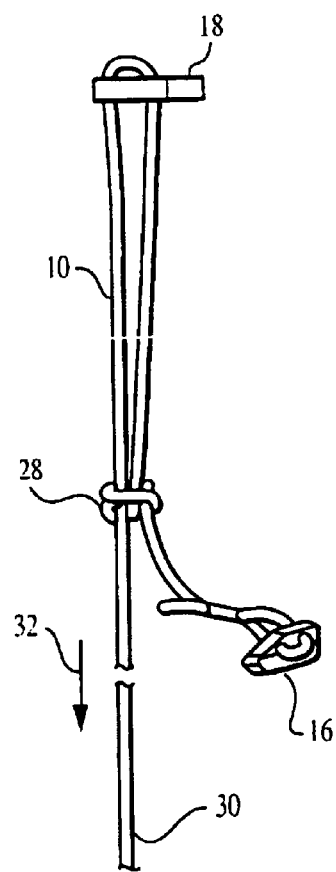

Referring to FIGS. 2E–2I, suture 10 is now attached to fixation member 18 by passing long suture section 52 through holes 18*a*, 18*b* in second fixation member 18 (FIG. 2E). Long suture section 52 now defines a first suture length 62 and second suture length 64. Slip knot 28 is formed by passing fixation member 16 under suture length 64, over suture length 64, and under suture length 62, forming a loop 66 (FIG. 2F); then passing fixation member 16 over suture lengths 62 and 64, forming a loop 68 (FIG. 2G); and then passing fixation member 16 under suture lengths 64 and 62 (FIG. 2G), and finally through loop 68 (FIG. 2H). Pulling fixation member 16 relative to fixation member 18 tightens slip knot 28 (FIG. 2I). Pulling free end 30 of suture 10 now acts to slide suture 10 through slip knot 28, while slip knot 28 limits sliding of suture 10 in the opposite direction when suture 10 is under tension.

Referring to FIG. 3, a delivery device 99 for implanting device 8 in tissue 14 includes a sheath 200 and a needle 100. Sheath 200 is preferably formed from plastic, and needle 100 is preferably metal. Needle 100 has an open distal end 111 with a pointed, tissue piercing tip 108. Needle 100 has an inner surface 102 defining a lumen 104 and a slot 110 both extending to open distal end 111. Slot 110 extends from an outer surface 106 of needle 100 to lumen 102. As described further below, needle 100 receives fixation member 16 and 18 within lumen 104 and slot 110 with suture 10 tied to fixation members 16, 18 as illustrated in FIGS. 2A–2I. Sheath 200 defines a lumen 202 which receives needle 100 and device 8 with suture 10 positioned between needle 100 and sheath 200 and extending through a hole 201 defined at a proximal end 203 of sheath 200. Sheath 200 has a distal end 202 from which needle 100 extends.

Referring also to FIGS. 4–4B, slot 110 has a proximal, closed end 120 and a distal open end 140. Fixation members 16 and 18 (which are generally described in U.S. Ser. No. 09/453,120, supra) have the same shape with each fixation member including a cylindrical region 151 received within lumen 104 of needle 100, and a fin 152 extending through slot 110 with a portion 154 of fin 152 extending beyond outer surface 106 of needle 100. Fixation member 16 is located at a distal region 112 of slot 110, and fixation member 18 is located at a proximal region 114 of slot 110. Distal end 111 of needle 100 is indented, for example, crimped at 150, and inner surface 102 of needle 100 has a protrusion extending into lumen 104, for example, a dimple 130, near distal end 140. Dimple 130 and crimp 150 are sized to resist unintentional passage of the fixation members either over dimple 130 or through open distal end 111, though only a small force on the fixation members is needed to overcome the resisting load applied to the fixation members by crimp 150 and dimple 130. Fixation members 16, 18 have sloped surfaces 152*a* which aid in passage through tissue, and a flat surface 154*a* which aid in retention of the fixation member at their deployment sites.

During manufacturing, to position fixation members 16, 18 in needle 100, after suture 10 is attached to fixation members 16, 18, fixation member 18 is loaded in needle 100 by passing fixation member 18 through distal end 111 and sliding fixation member 18 along lumen 104 and slot 110 to proximal end 120 of slot 110. Fixation member 16 is then loaded in needle 100 by passing fixation member 16 through distal end 111 and positioning fixation member 16 in region 112. Dimple 130 and crimp 150 are then formed. Fixation member 16 is now restrained from unintentional movement in the proximal direction by dimple 130 and in the distal direction by crimp 150. Alternatively, as shown in FIG. 4C, rather than dimple 130, a needle 100*a* includes a ramp 130*a* formed by making three slits in a wall 101 of needle 100*a* and bending a section of the wall toward the inside of the needle.

Figure 5:
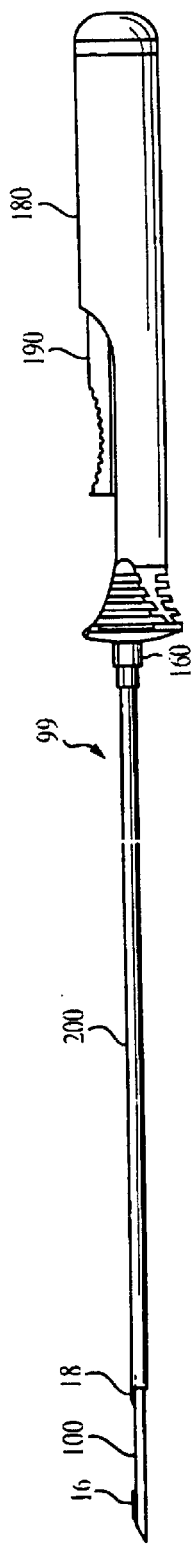
FIG. 5 is side view of the delivery device of FIG. 3.

Referring also to FIG. 5, needle 100 has a proximal end 160 mounted to a handle 180. Located within needle 100, proximal of fixation member 18, is a push rod 170 (FIG. 4) used to advance fixation member 18, as described below. Handle 180 includes an actuating slider 190 attached to push rod 170 for advancing push rod 170. Once device 8 is secured to needle 100, as described above, sheath 200 is placed over needle 100, with the majority of suture 10 located within and protected by sheath 200. Sheath 200 also covers the majority of fixation member 18 and helps keep fixation member 18 in position. Sheath 200 is then secured to handle 180 by an interference fit. The distance needle 100 extends from sheath 200 determines the penetration depth of needle 100 into the tissue. Delivery device 99 is supplied to the surgeon with device 8 pre-loaded in needle 100.

Figure 5A:
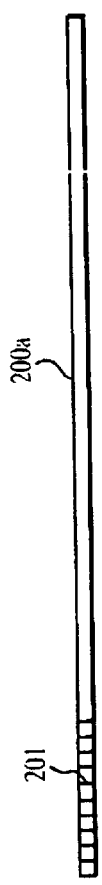
FIG. 5A is a side view of a variable length depth stop for use with the delivery device of FIG. 3.

Referring to FIG. 5A, an outer protective tube 200*a* can be placed over sheath 200. Tube 200*a* protects the needle tip during shipping. If it is desired to supply the surgeon with a variable length depth stop, tube 200*a* can be provided with gradations 201. The surgeon scores tube 200*a* to provide the tube with the desired length for the surgical procedure. Tube 200*a* is coupled to handle 190 by a loose interference fit to allow the surgeon to remove tube 200*a* if tube 200*a* is not being used during surgery.

Figure 5B:
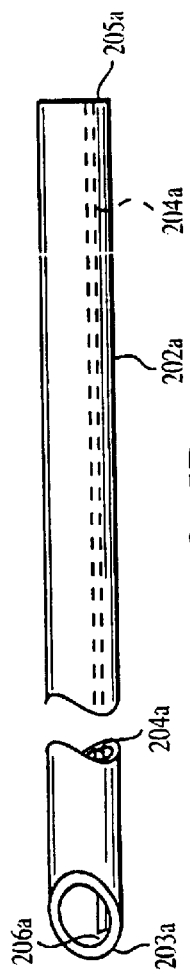
FIG. 5B is a perspective view of a cannula for use with the delivery device of FIG. 3.
Figure 6:
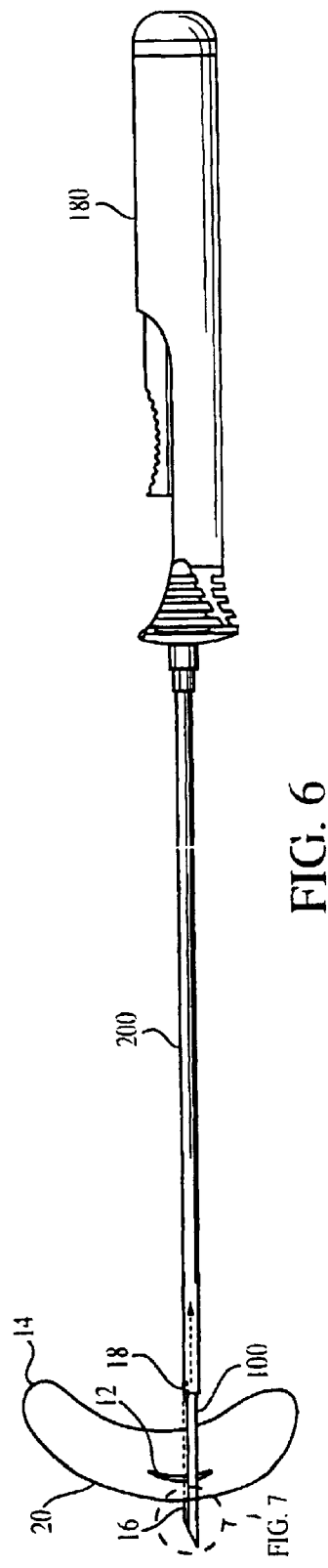
FIGS. 6–11 show the delivery device in use inserting the closure device of FIG. 1 in soft tissue, with FIG. 7 being an exploded view of region 7 of FIG. 6.

Referring to FIG. 5B, to eliminate the need for placement of delivery device 99 through an arthroscopy cannula, a removable cannula 202*a*, formed, for example, of a plastic material, can be placed over sheath 200. Cannula 202*a* has a distal, tissue penetrating tip 203*a* and a slot 204*a* extending from a proximal end 205*a* of cannula 202*a* to within about 0.02 inches of distal tip 203*a* to define a distal region 206*a*. Slot 204*a* permits the removal of cannula 202*a* from delivery device 99 after placement of the delivery device in the joint. To remove cannula 202*a*, the surgeon grasps the cannula and moves it laterally relative to sheath 200, until sheath 200 slides through slot 204*a*. The surgeon then pulls cannula 202*a* proximally, which breaks cannula region 206*a*, permitting complete removal of cannula 202*a*.

Figure 7:
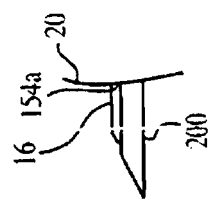
Figure 8:
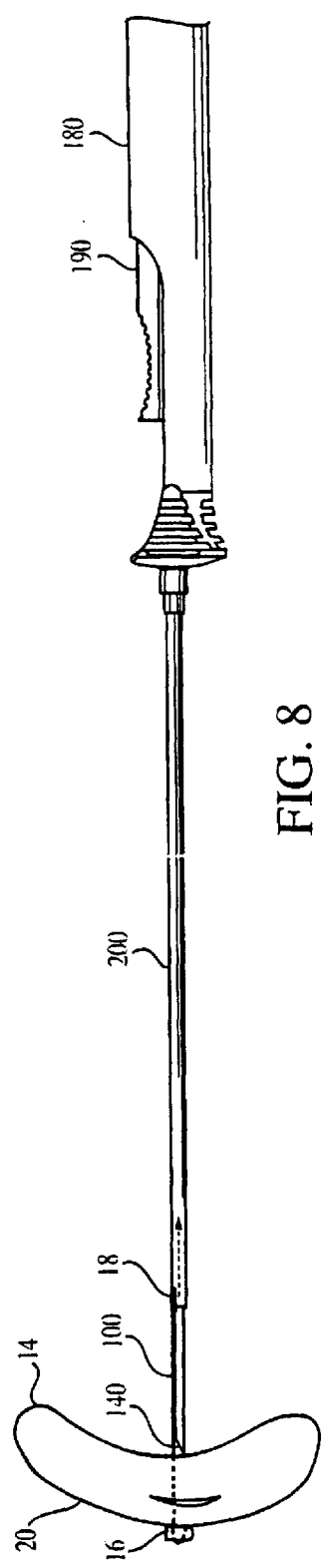

Referring to FIGS. 6–11, in use, preferably under arthroscopic guidance, the user inserts delivery device 99 into, for example, the knee joint, and passes needle 100 through soft tissue 14 and across tear 12, until needle tip 108 and fixation member 16 extend through tissue surface 20. Dimple 130 prevents fixation member 16 from sliding proximally in response to forces acting on fixation member 16 during insertion through tissue 14. Fixation member 16 is now positioned with flat, tissue facing surface 154*a* of portion 154 of fin 152 extending beyond needle surface 106 engaging tissue surface 20 (FIG. 7). The user then pulls delivery device 99 proximally removing needle 100 from tissue 14 (FIG. 8). The force of the engagement of fixation member 16 with tissue surface 20 during removal of needle 100 overcomes the retention force of crimp 150. Fixation member 16 slides distally out of open end 111 of needle 100 and remains at surface 20. During the retraction of needle 100, a portion of suture 110 with knot 28 is played out of delivery device 99, with suture 10 extending through soft tissue 14 across tear 12.

Figure 9:
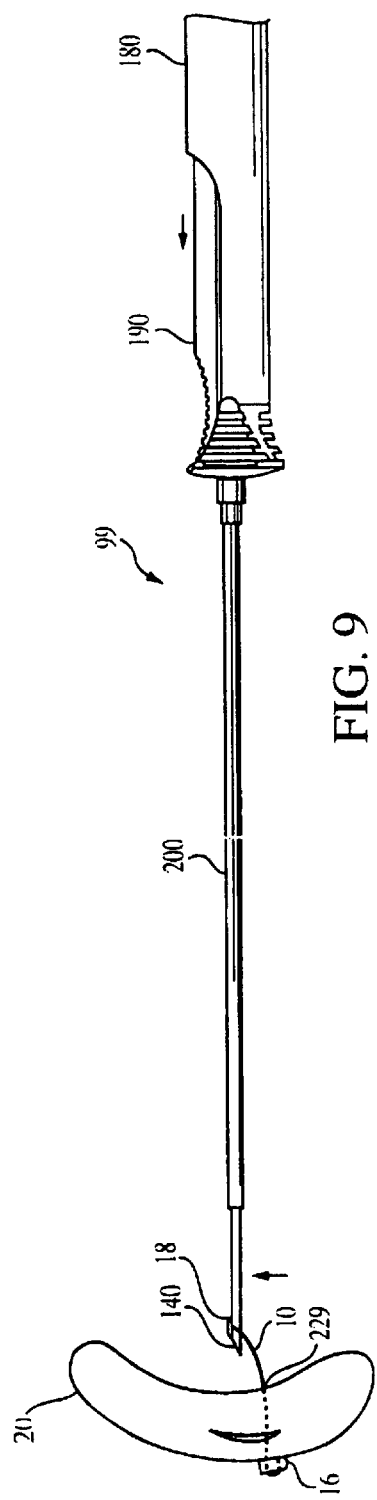
Figure 11:
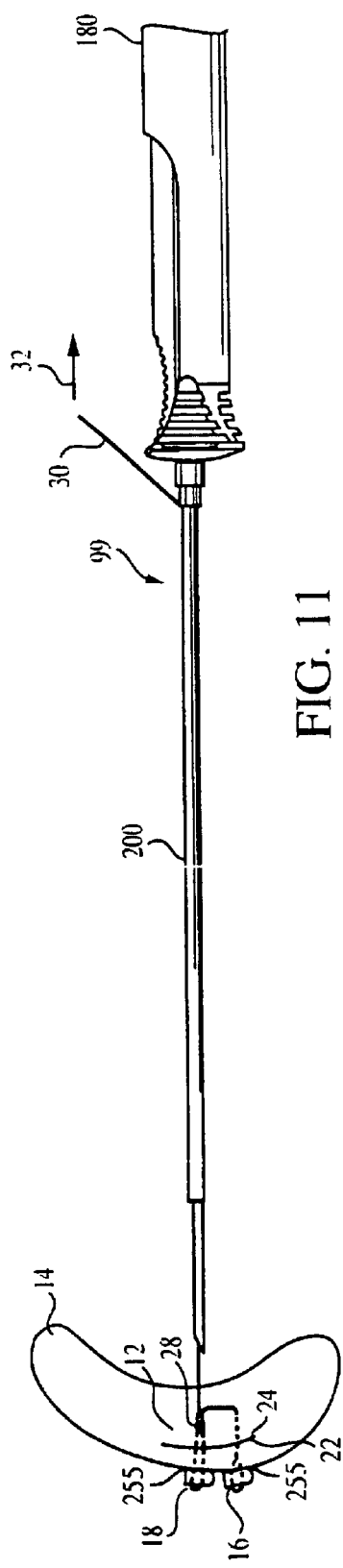

The user then advances slider 190, advancing rod 170 to push fixation member 18 distally, over dimple 130, to reside in region 112 between dimple 130 and crimp 150 (FIG. 9). The user then moves needle 100 to a spaced location to the side of exit point 229 of suture 10 from tissue 14, and re-inserts needle 100 into soft tissue 14, across tear 12, and through surface 20, until needle tip 108 and fixation member 18 extend through tissue surface 20 (FIG. 10). The user then pulls delivery device 99 proximally removing needle 100 from tissue 14 (FIG. 11). The force of the engagement of fixation member 18 with tissue surface 20 during removal of needle 100 overcomes the retention force of crimp 150 such that fixation member 18 slides distally out of open end 111 of needle 100 and remains at surface 20, as described above with reference to fixation member 16.

Free end 30 of suture 10 extends from sheath 200, as shown in FIG. 11. The user grasps free end 30 of suture 10 with forceps or by hand and pulls on free end 30 of suture 10. This shortens the length of suture between fixation members 16 and 18 (suture portions 10a–10c), bringing sides 22, 24 of tear 12 into juxtaposition, as shown in FIG. 11. When free end 30 of suture 10 is pulled, slip knot 28 moved closer to fixation member 18. Depending on the length of suture between fixation members 16 and 18, slip knot 28 will either be on tissue surface 26 or move within tissue 14. Slip knot 28 allows suture 10 to slide in the direction of arrow 32, but does not allow suture 10 to slide in the opposite direction. The tension placed on suture 10 by pulling on the suture relative to fixation members 16, 18, acts to turn the fixation members such that their long sides 255 are in contact with tissue surface 20. Excess suture 10 can then be cut off. Further manipulation of suture 10 is not needed to secure fixation members 16, 18, although the surgeon may wish to provide additional fastening as a back-up securement measure.

Alternative Embodiments

Figure 12:
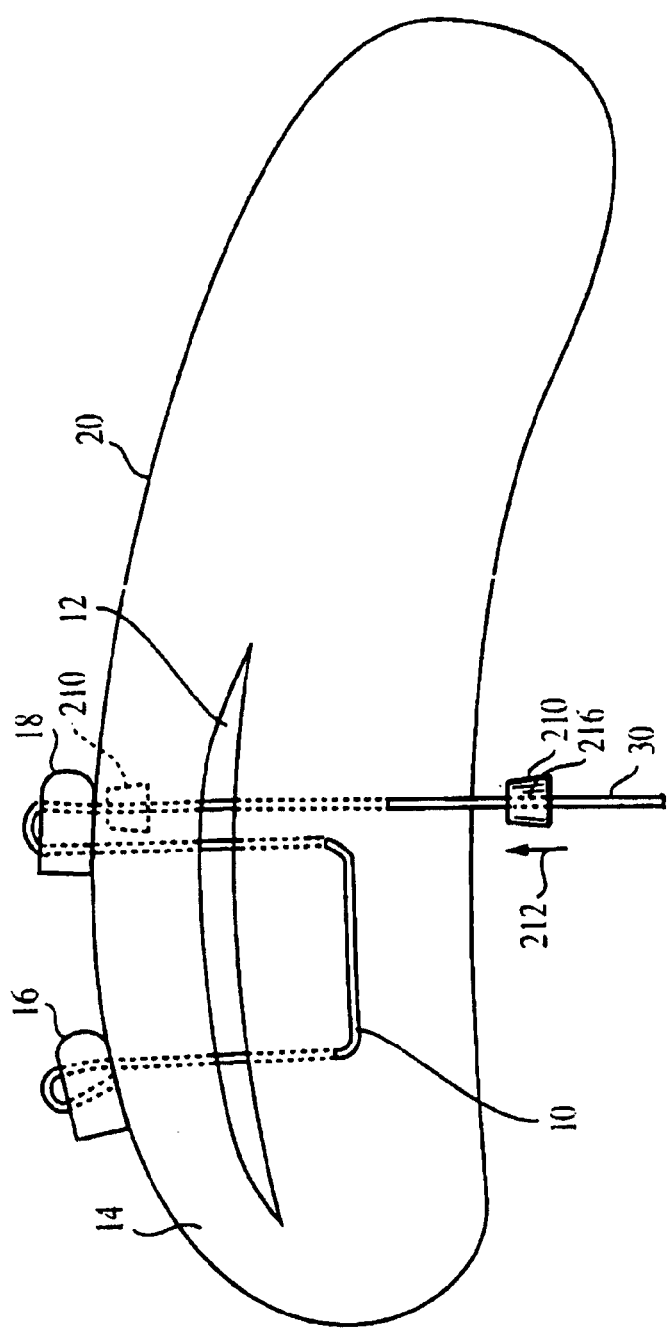
FIG. 12 is an illustration of the closure device of FIG. 1 with an alternative embodiment of a retaining element, shown mending a tear in soft tissue.

Referring to FIG. 12, rather than a slip knot 28 acting as a retaining element allowing suture 10 to be tightened while resisting loosening of suture 10, here, a separate retaining element 210 is positioned on free end 30 of suture 10. While pulling on free end 30, the surgeon advances retaining element 210 through tissue 14, in the direction of arrow 212, until retaining element 210 is positioned against fixation member 18, as shown in dashed line. This action acts to close tear 12 and secure device 8 in place.

Retaining element 210 defines a through bore 216 for receiving suture 10. The material of retaining element 210, e.g., acetal, is selected, and the diameter of through bore 216 is sized relative to suture 10 to provide the desired amount of friction between suture 10 and retaining element 210 for adequate securement. Thus, the user can slide suture 10 in the direction of arrow 212, but adequate friction is provided between suture 10 and retaining element 210 to limit sliding of retaining element 210 in the opposite direction under normal loads in the knee joint.

Figure 12C:
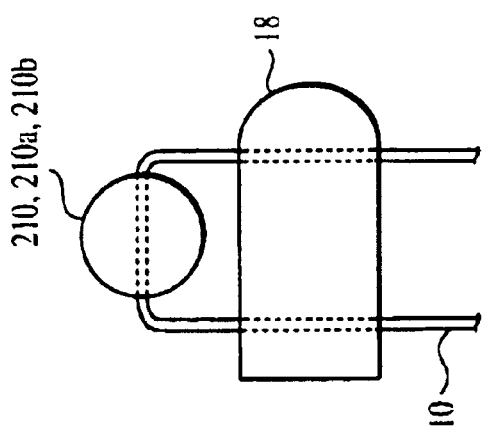
FIG. 12C shows the retaining element of FIG. 12 in an alternative position.
Figure 12B:
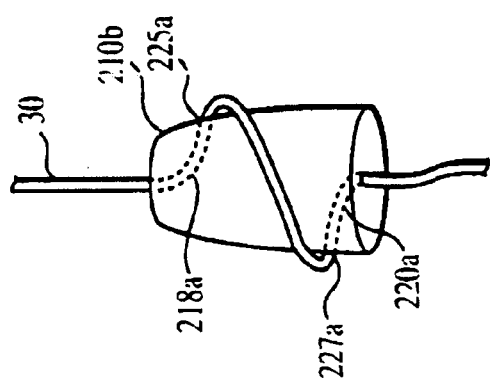
FIGS. 12A and 12B show alternative embodiments of the retaining element of FIG. 11.
Figure 12A:
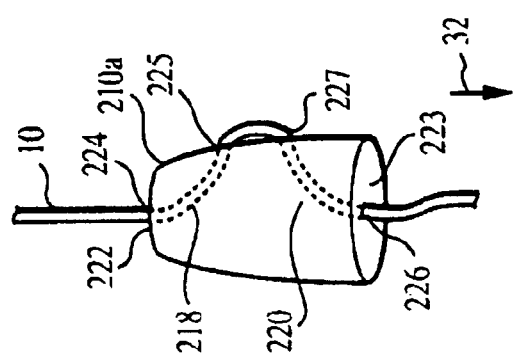

Referring to FIG. 12A, a retaining element 210a defines two angled channels 218, 220 for receiving free end 30 of suture 10. Retaining element 210a has a generally cylindrical surface 221 and ends 222, 223. Channel 218 has a first opening 224 at end 222 and second opening 225 on surface 221. Channel 220 has a first opening 226 at end 223 and a second opening 227 on the same side of surface 221 as channel 218. Suture 10 follows a tortuous path through channel 218, over surface 221 between openings 225 and 227, and then through channel 220 with free end 30 extending from opening 226. The tortuous path aids in securement of device 8.

In FIG. 12B, rather the channel opening on surface 221 being on the same side, a retaining element 210b defines two angled channels 218a, 220a each having a channel end 225a, 227a, respectively, on opposite sides of surface 221. Suture 10 thus wraps part way around element 210b to aid in securement of device 8.

Referring to FIG. 12C, rather than positioning the retaining element on suture 10 after suture 10 exits from fixation member 18, here retaining element 210, 210a, or 210b is positioned along suture 10 between the portions of suture 10 passing through fixation member 18.

Retaining elements 210, 210a, 210b are slidably received on suture 10. In the embodiments of FIGS. 12–12B, the retaining element slides over suture 10, changing position relative to fixation member 18, while in the embodiment of FIG. 12C, suture 10 slides within the retaining element with the position of the retaining element being relatively unchanged relative to fixation member 18.

Figure 13:
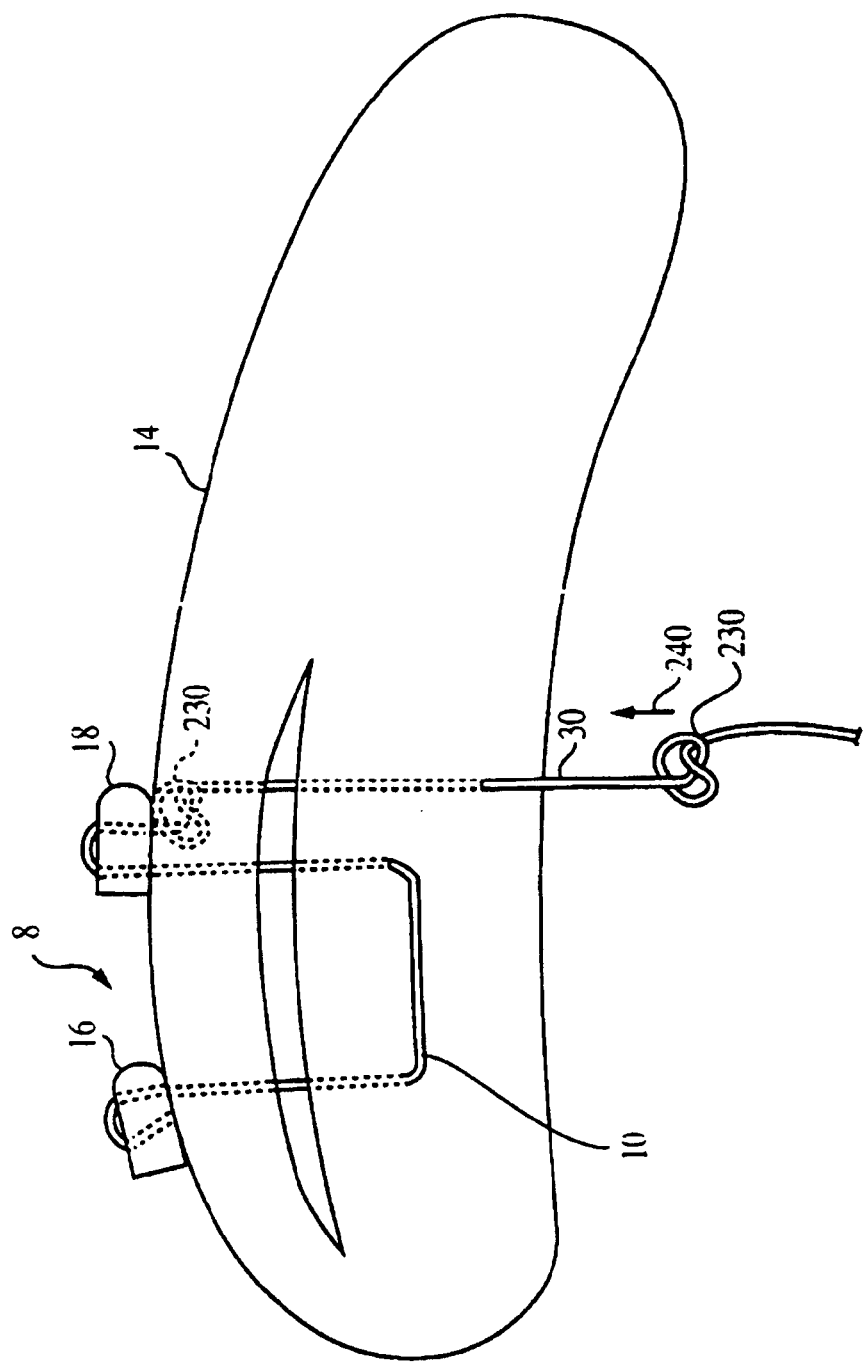
FIG. 13 shows an additional alternative embodiment of a retaining element in the form of an overhead knot.
Figure 13B:
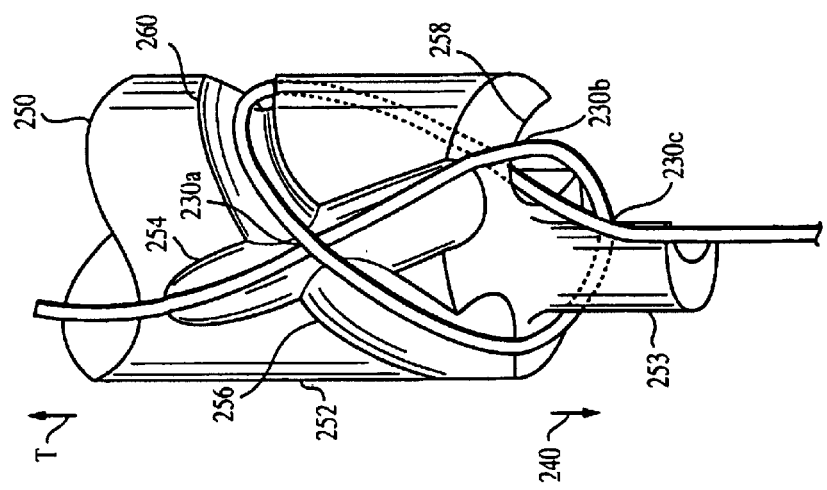
FIGS. 13A and 13B show an overhand knot and a knot pusher for advancing the overhand knot of FIG. 13.
Figure 13A:
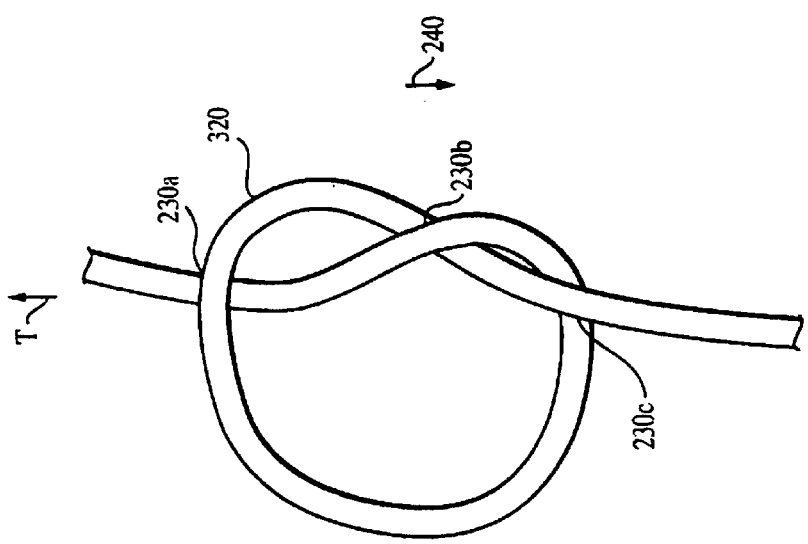

Referring to FIG. 13, device 8 can be secured to tissue 14 using a simple overhand knot 230. Knot 230 is first tied in free end 30 of suture 10 and pushed, in the direction of arrow 240, through tissue 14 and against fixation member 18, as shown in dashed line. Referring to FIGS. 13A and 13B, knot 230 includes three crossing points, labeled, 230a, 230b, and 230c. When under tension, T, knot 230 tends to tighten upon itself, rather than slide in the direction of arrow 240 making it difficult to advance knot 230 along suture 10. To enable tension, T, to be applied to suture 10 at the same time knot 230 is advanced in the direction of arrow 240, a knot pusher 250 is used. Knot pusher 250 is configured to keep suture at crossing points 230a, 230b, and 230c from touching, such that knot 230 does not tighten upon itself under tension, T. This permits knot 230 to slide along the tensioned suture when knot pusher 250 is advanced in the direction of arrow 240.

Knot pusher 250 has a cylindrical body 252 and an end post 253. Body 252 defines a first groove 254 and a second groove 256 on one surface, and a third groove 258 that is an extension of groove 256 on an opposite surface. Grooves 254 and 256 form and X pattern, and grooves 256 and 258 define a loop 260 extending around body 252. The three grooves differ in depth, with groove 256 being the shallowest and groove 258 being the deepest. Thus, when suture 10 is formed into an overhand knot and positioned within grooves 254, 256, and 258, the suture at crossing points 230a, 230b, and 230c does not touch. Once knot 230 is advanced against fixation member 18, knot pusher 250 is removed by pulling retrograde on the knot pusher. To aid in removal of knot pusher 250, a tube (not shown) can be advanced over knot pusher 250 between the knot pusher and the suture. As the tube is advanced past suture crossing point 230a, the suture is stripped from knot pusher 250.

Figure 14:
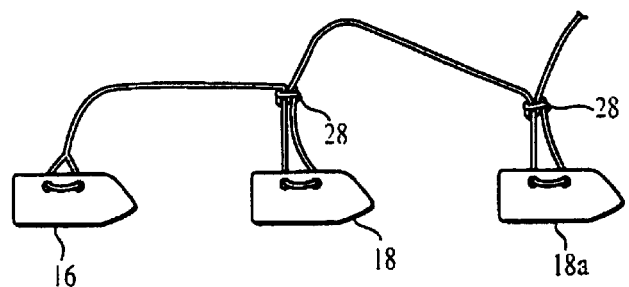
FIG. 14 is an illustration of an alternative embodiment of a closure device.

Referring to FIG. 14, one or more additional fixation members 18a with a slip knot 28 formed in suture 10 can be added to device 8. In use, fixation members 16 and 18 are implanted as described above, with suture 10 being tightened to secure fixation members 16 and 18 in place. Additional fixation member 18*a* is then implanted and suture 10 tightened to secure fixation member 18*a* in place. To accommodate additional fixation members, slot 110 in needle 100 of delivery device 99 is extended. To permit access to fixation member 18 by push rod 170, additional fixation members 18*a* preferably include a through bore (not shown) for passage therethrough by push rod 170. Push rod 170 preferably is biased off angle such that when push rod 170 is pulled out of the passage in fixation member 18*a*, the push rod is no longer aligned with the passage. Subsequent advancement of push rod 170 then engages an end face of fixation member 18*a* to push the fixation member toward the tip of the needle 100, rather than back through the passage. Slider 190 is preferably spring loaded such that after fixation member 18 is pushed out of needle 100, push rod 170 springs back to engage the next fixation member 18*a*.

Figure 14A:
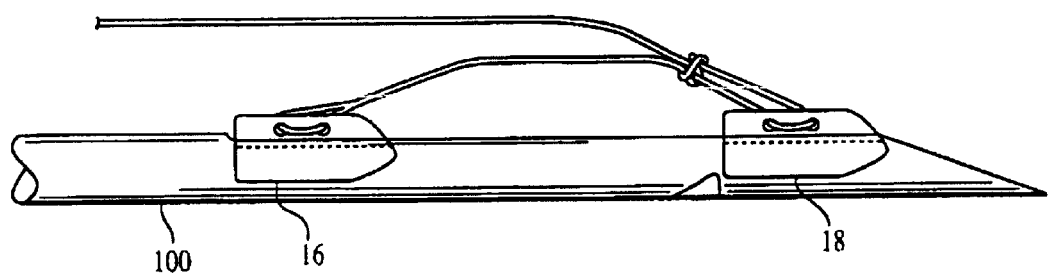
FIG. 14A shows an alternative arrangement of the closure device and delivery device of FIG. 4.
Figure 14B:
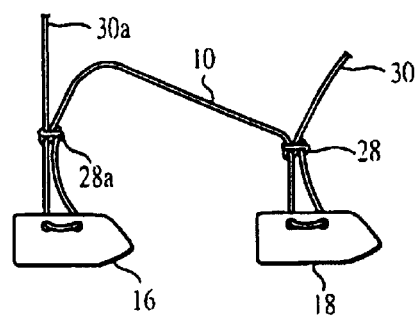
FIG. 14B is an illustration of an alternative embodiment of a closure device.

Referring to FIG. 14A, the positions of fixation member 16 and 18 in needle 100 can be swapped, with fixation member 18 located in distal region 112 such that fixation member 18 is implanted in the tissue prior to implantation of fixation member 16. Referring to FIG. 14B, rather than suture 10 being fixed to fixation member 16, here suture 10 is attached to fixation member 16 the same as the attachment to fixation member 18, such that a second slip knot 28*a* is formed and a second free end 30*a* of suture extends from fixation member 16. To secure fixation members 16 and 18, both ends 30 and 30*a* of suture 10 are pulled.

Figure 15:
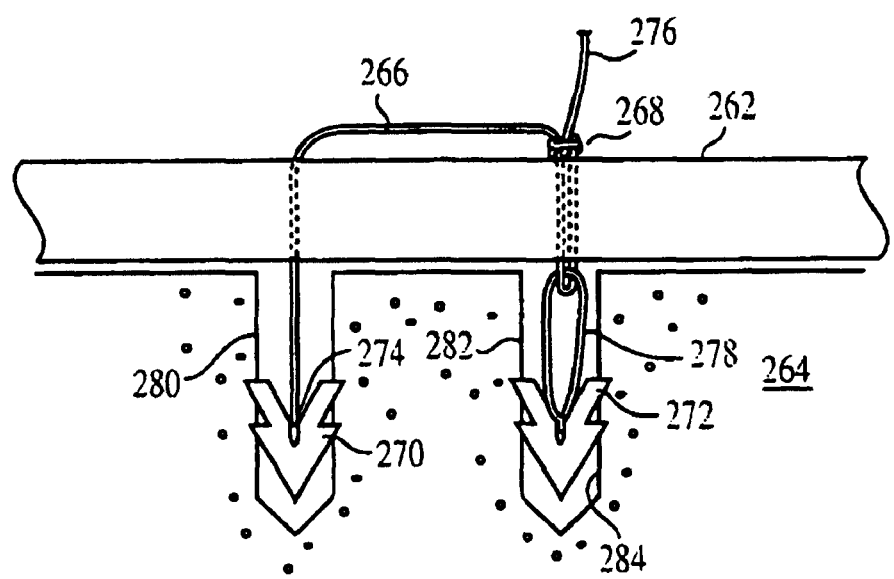
FIG. 15 is an illustration of an alternative embodiment of a closure device for use in attaching soft tissue to bone.

Referring to FIG. 15, in an application for securing soft tissue 262 to bone 264, a suture 266 is attached to fixation members in the form of a first anchor member 270 and a second anchor member 272. Members 270, 272 are, for example, TAG WEDGE bone anchors available from Smith & Nephew, Inc. Endoscopy Division, Andover, Mass. Other bone anchors known in the art can be employed. Suture 266 has a first end 274 fixed to anchor member 270, a second free end 276, and a slip knot 268, formed as described above for slip knot 28. Suture 266 preferably passes through a separate suture loop 278, rather than through 272 itself. Suture loop 278 acts as a good pulley allowing suture 266 to slide relative to suture loop 278.

In use, the user forms bone holes 280, 282 in bone 264. The user then implants anchor member 270 in bone hole 280, with suture 266 already threaded as shown, followed by implanting anchor member 272 in bone hole 282. The user then pulls on free end 276 of suture 266, which brings soft tissue 262 against bone 264. Slip knot 268 limits loosening of suture 266. By using suture loop 278, suture 266 is not located within bone hole 282 in use thus limiting the possibility of trapping suture 266 against wall 284 of bone hole 282. If suture 266 were trapped in bone hole 282, pulling free end 276 of suture 266 would not result in shortening the length of suture between anchors 270, 272, which acts to secure soft tissue 262 against bone 264.

Figure 16:
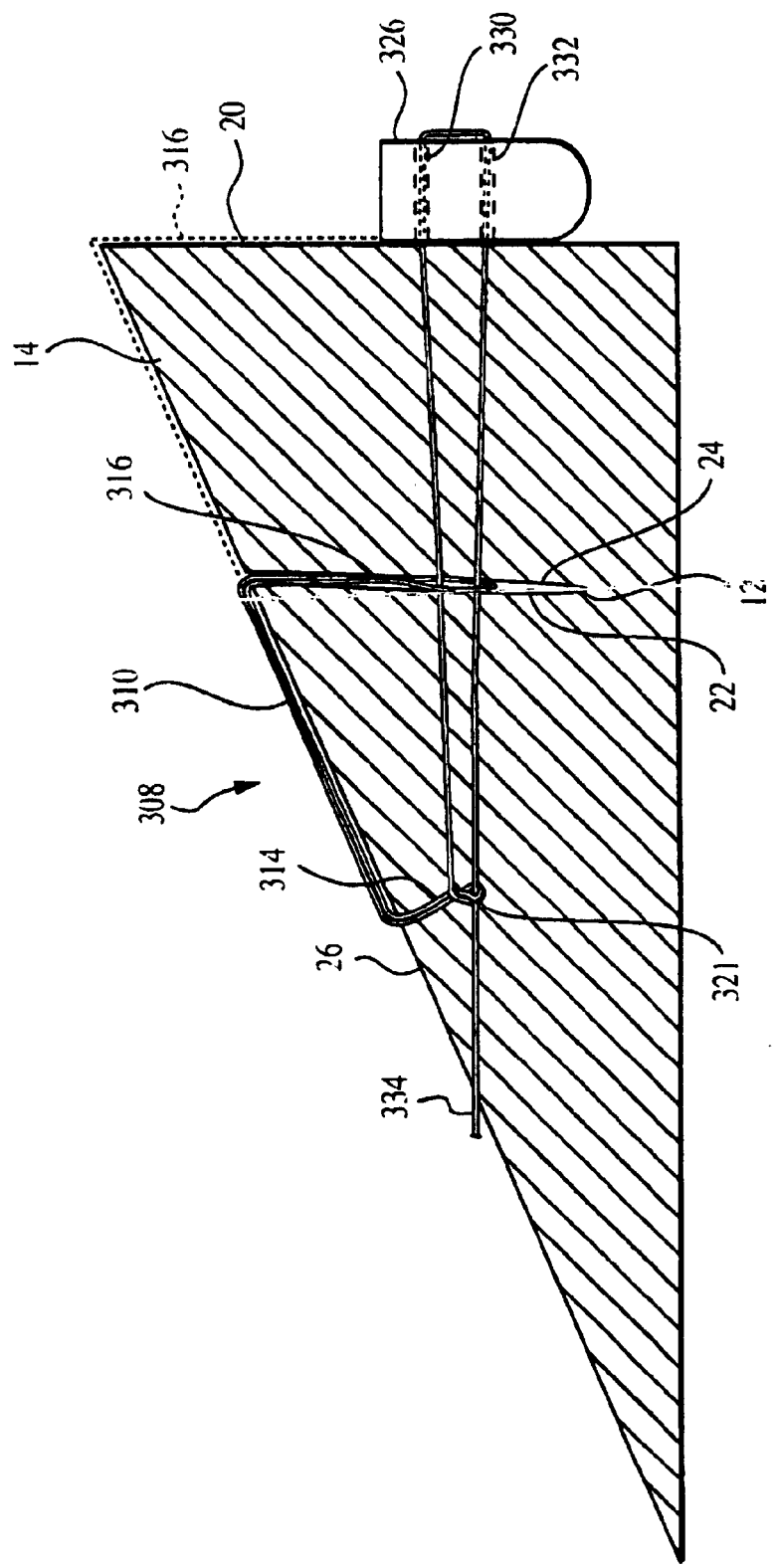
FIG. 16 is a cross-sectional side view of an alternative embodiment of a closure device, shown mending a tear in soft tissue.
Figure 18:
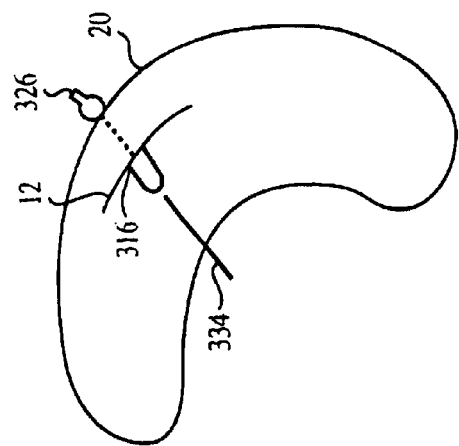
FIG. 18 is a top view of the closure device of FIG. 16, shown after securing the closure device in place.
Figure 17:
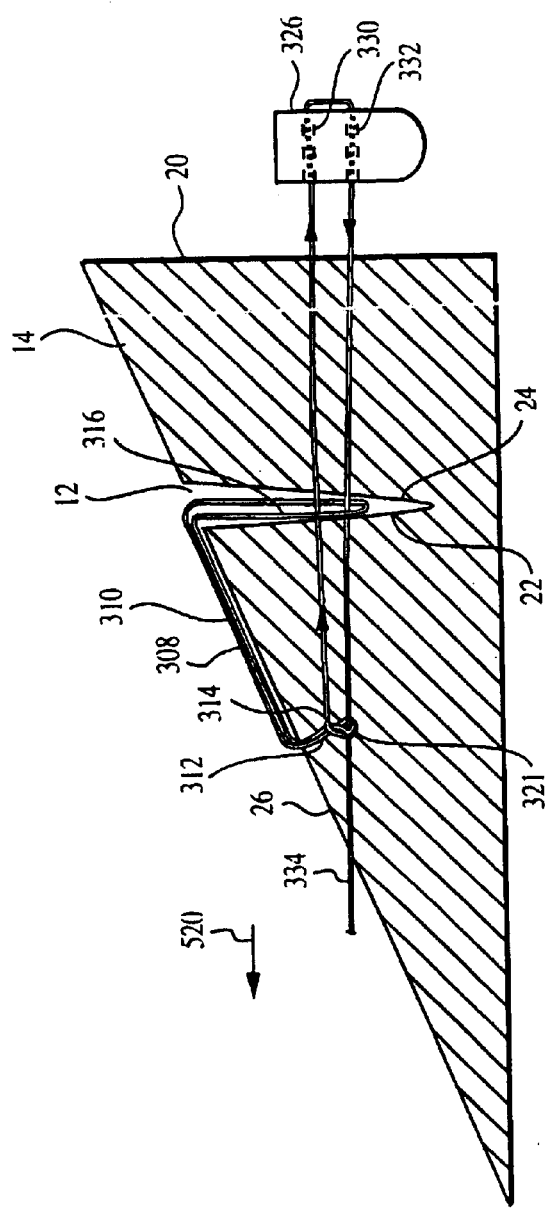
FIG. 17 shows the closure device of FIG. 16 in use prior to securing the closure device in place.

Referring to FIGS. 16–18, a device 308 for repairing a tear 12 in tissue 14 includes a suture 310 attached to a single fixation member 326. Fixation member 326 defines through holes 330, 332 for receiving suture 310. Suture 310 has a first end 312 attached to suture 310 at point 314 (as described above with reference to FIG. 2B) to form a looped end 316 remote from fixation member 326, and a second, free end 334.

When implanted in the knee joint, fixation member 326 lies on a surface 20 of tissue 14. Looped end 316 is located in tear 12 and extends along surface 26 of tissue 14. Suture 310 extends through tissue 14, passing through looped end 316 in tear 12, and emerging at tissue surface 20 where suture 310 loops through fixation member 326. Suture 310 extends back through tissue 14, passing through looped end 316 in tear 12 and through a slip knot 321 formed in suture 310, and emerging at tissue surface 26. As described further below, after device 308 is positioned in tissue 14, the user pulls on free end 334 of suture 310, in the direction of arrow 520, to bring sides 22, 24 of tear 12 together into juxtaposition (as shown in FIG. 16). Slip knot 321 limits loosening of suture 310. Alternatively, looped end 316 is located on surface 20 between fixation member 326 and surface 20, as shown in dashed line in FIG. 16.

Figure 19:
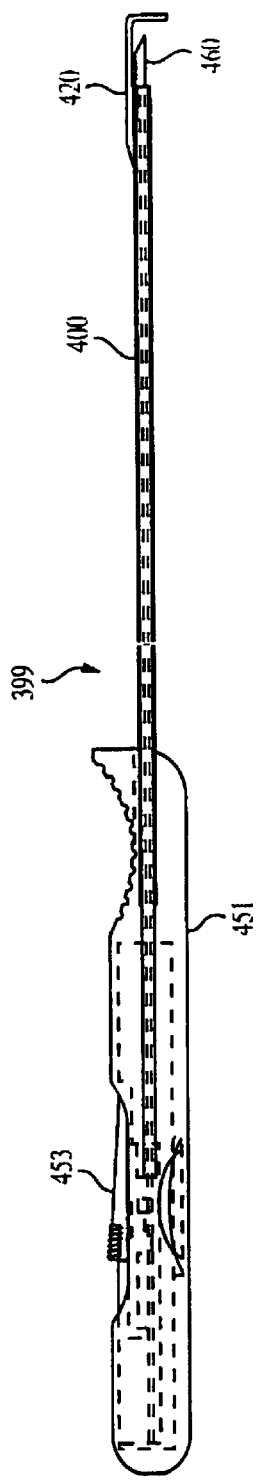
FIG. 19 is a side view of a delivery device for inserting the closure device of FIG. 16 in soft tissue.
Figure 19A:
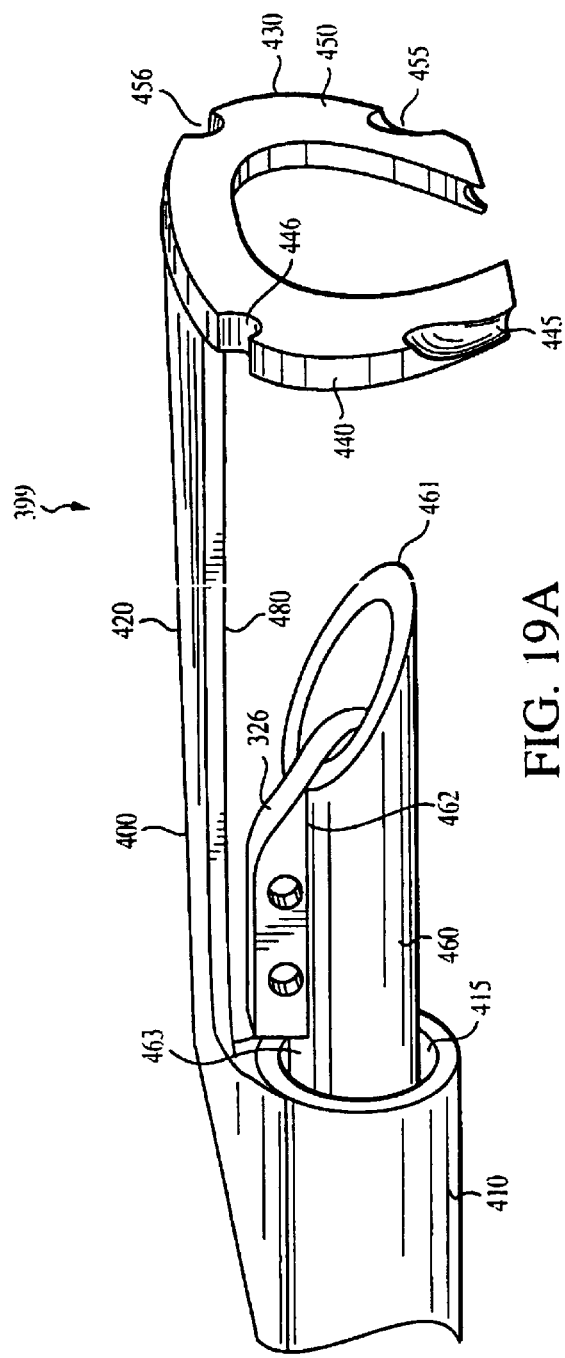
FIG. 19A is a perspective view of a distal section of the delivery device of FIG. 19 shown with a fixation member of the closure device of FIG. 16.

Referring to FIGS. 19–19B, a delivery device 399 for implanting device 308 includes a suture holder 400 and needle 460. Suture holder 400 includes a tube 410 defining a lumen 415 through which needle 460 extends, a shaft 420, and a distal portion 430. Distal portion 430 has a first tine 440 defining grooves 445 and 446, and a second tine 450 defining grooves 455, 456. Needle 460 has a beveled tip 461 and a slot 462 in a top portion 463 of needle 460.

When assembled, fastening member 326 with attached suture 310 is positioned in slot 462 with suture 310 preformed with looped end 316 and slip knot 321. Slip knot 321 is formed as described above with reference to FIGS. 2A–2I, though where fixation member 16 is positioned in FIGS. 2A–2I, suture 310 is formed as looped end 316 (FIG. 19C). Looped end 316 is positioned on suture holder 400 within grooves 445, 446, 455 and 456 of tines 440, 450 (FIG. 19B), and extends along a bottom side 480 of shaft 420. As shown in FIG. 19, delivery device 399 includes a handle 451 with a push knob 453 for advancing needle 460 relative to suture holder 400.

Figure 20:
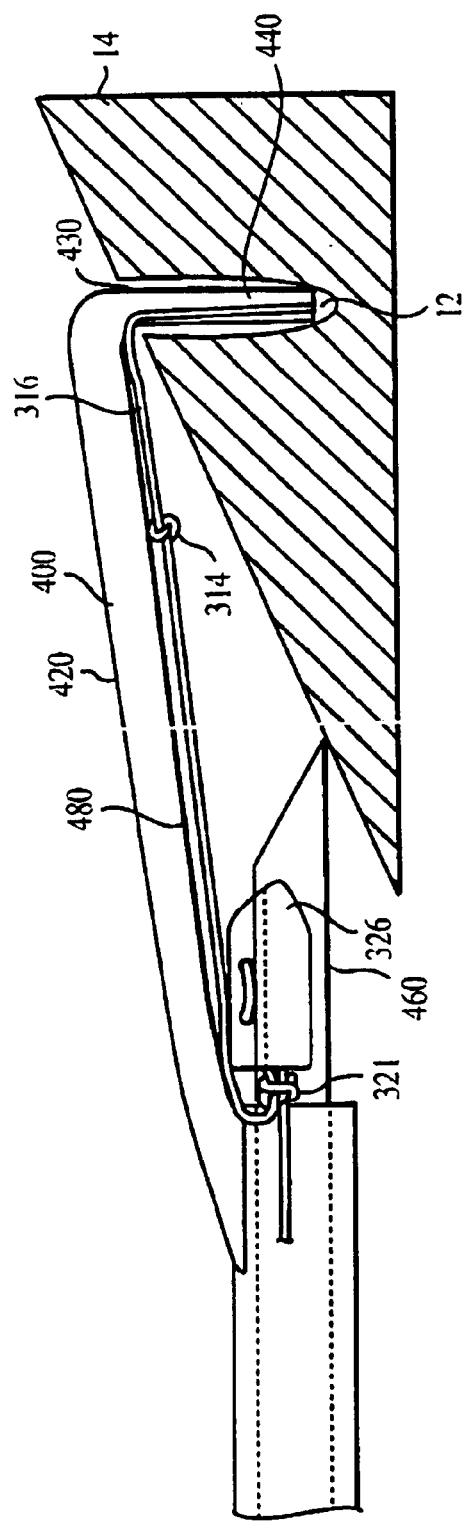
FIGS. 20–22 show the delivery device of FIG. 19 in use inserting the closure device of FIG. 16 in soft tissue.
Figure 21:
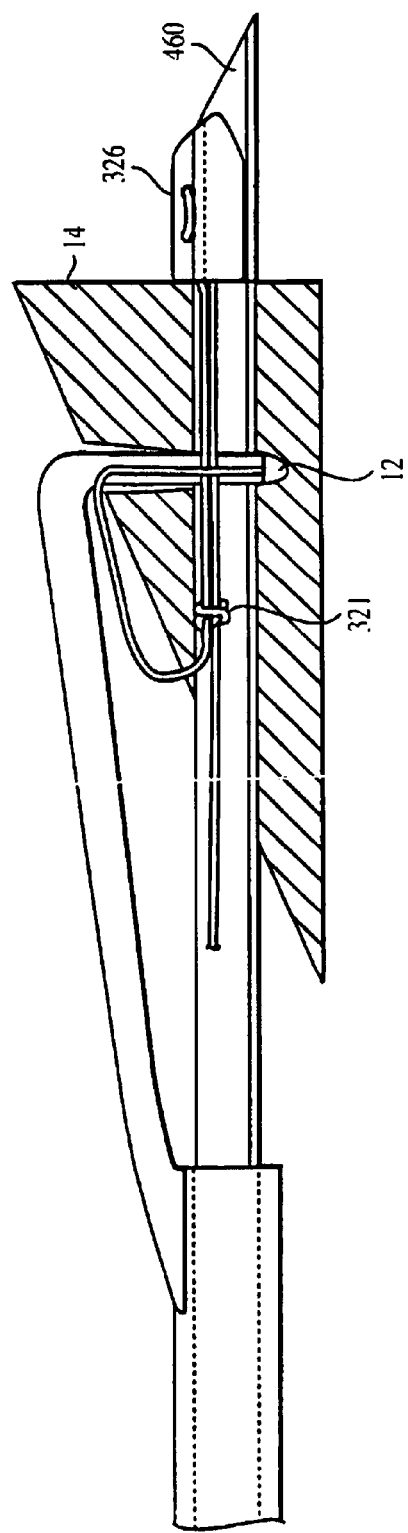
Figure 22:
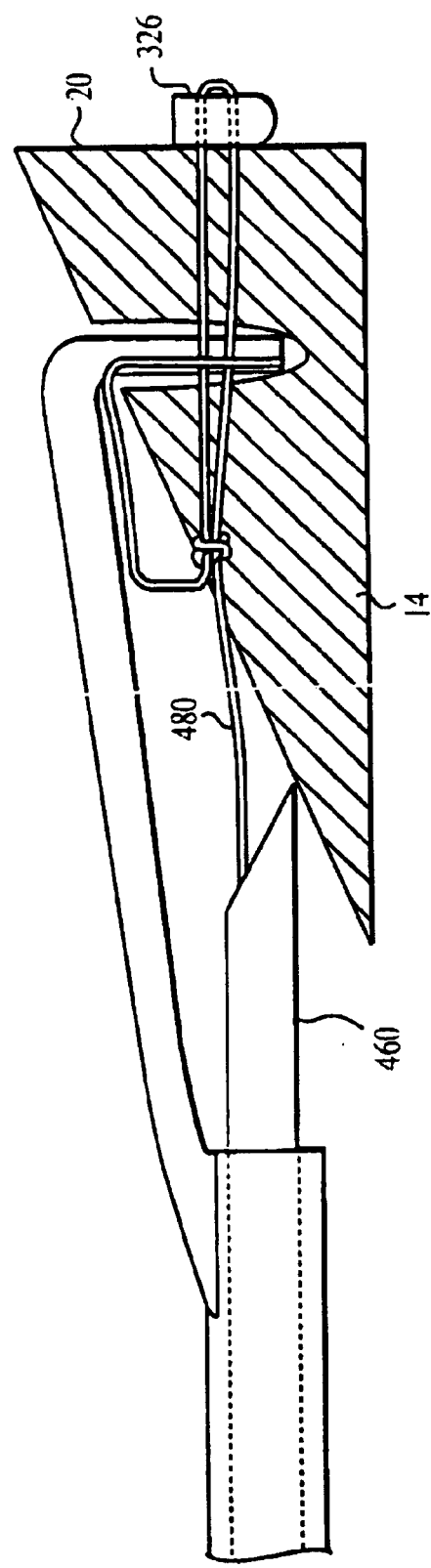

Referring to FIG. 20, in use, the user inserts distal portion 430 of suture holder 400 into tear 12 of tissue 14, and then advances needle 460 through tissue 14, traversing tear 12, and exiting tissue 14 at tissue surface 20. Needle 460 passes between tines 440 and 450, and thus through looped end 316 of suture 310 (FIG. 21). The user then retracts needle 460 from tissue 14 (FIG. 22). The contact of fastening member 326 with tissue surface 20 during the retraction of needle 460 acts to push fastening member 326 out of needle 460 such that fastening member 326 remains at surface 20, as described above with reference to FIG. 7. Pulling on free end 334 of suture 310 brings sides 22, 24 of tear 12 into juxtaposition. Slip knot 321 secures device 308 in place. Excess suture 310 can then be cut off.

Figure 23:
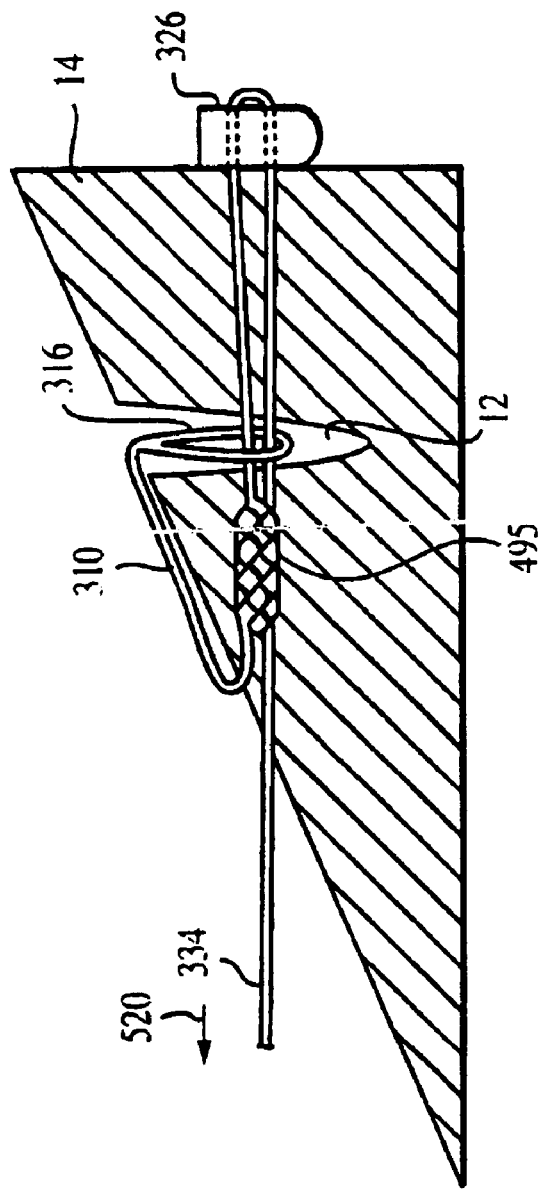
FIG. 23 is a cross-sectional side view of the closure device of FIG. 16 with an alternative embodiment of a retaining element, shown mending a tear in soft tissue.

Referring to FIG. 23, rather than securing device 308 with a slip knot, suture 310 includes a retaining element in the form of a Chinese trap or hand cuff 495, that is, an element that when pulled on, tightens around something disposed within the element. Free end 334 of suture 310 is slidably received within trap 495. When free end 334 of suture 310 is pulled in the direction of arrow 520 trap 495 is stretched, eventually gripping suture passing therethrough to secure suture 310 and device 308. The retaining element can also take the form of retaining elements described above with reference to FIGS. 12–12C and 13.

Figure 24:
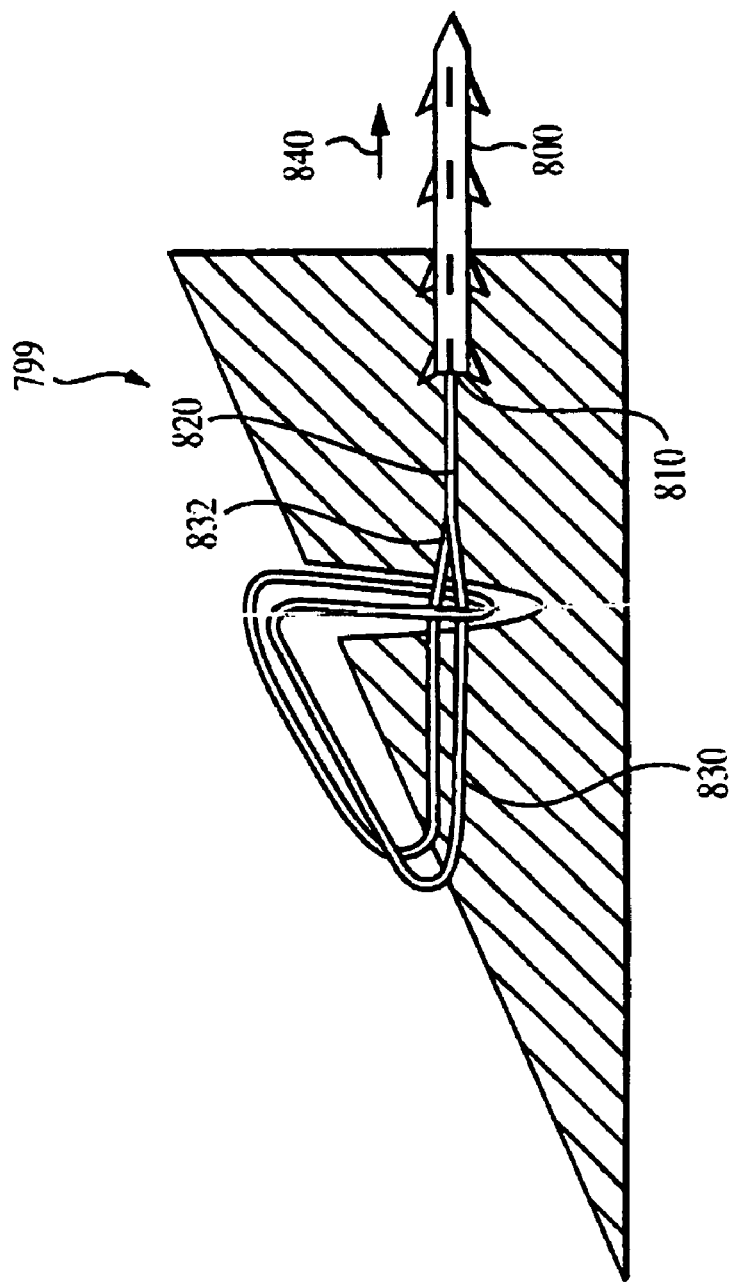
FIG. 24 is a cross-sectional side view of an alternative embodiment of a closure device, similar in use to the closure device of FIG. 16.

Referring to FIG. 24, a device 799 for repairing tear 12 in tissue 14 includes a barbed fastening member 800 and a suture 820. Suture 820 has an end 810 attached to fastening member 800. Suture 820 is formed in loop 830 with a second end 832 of suture 820 attached to suture 820. Delivery device 399 can be used to deploy device 799 with suture 820 being tightened to close tear 12 by pushing fastening member 800 in the direction of arrow 840, rather than pulling on a free end of suture. Barbed fastening member 800 limits loosening of suture 820.

Figure 25:
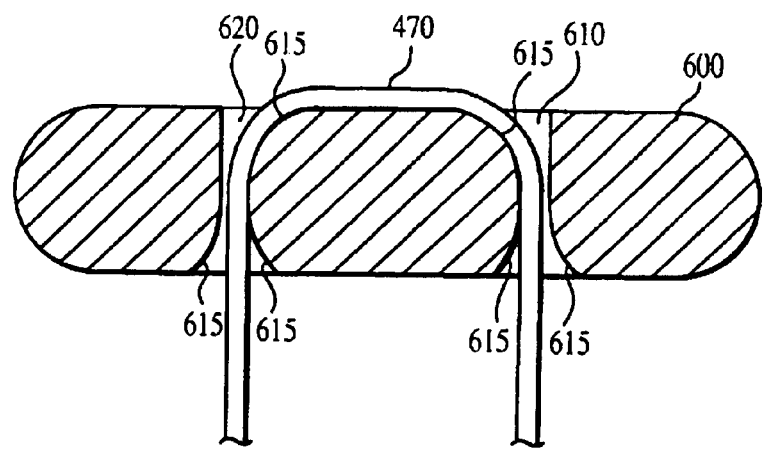
FIGS. 25 and 26 are alternative embodiments of a fixation member of the closure device of FIG. 16.
Figure 26:
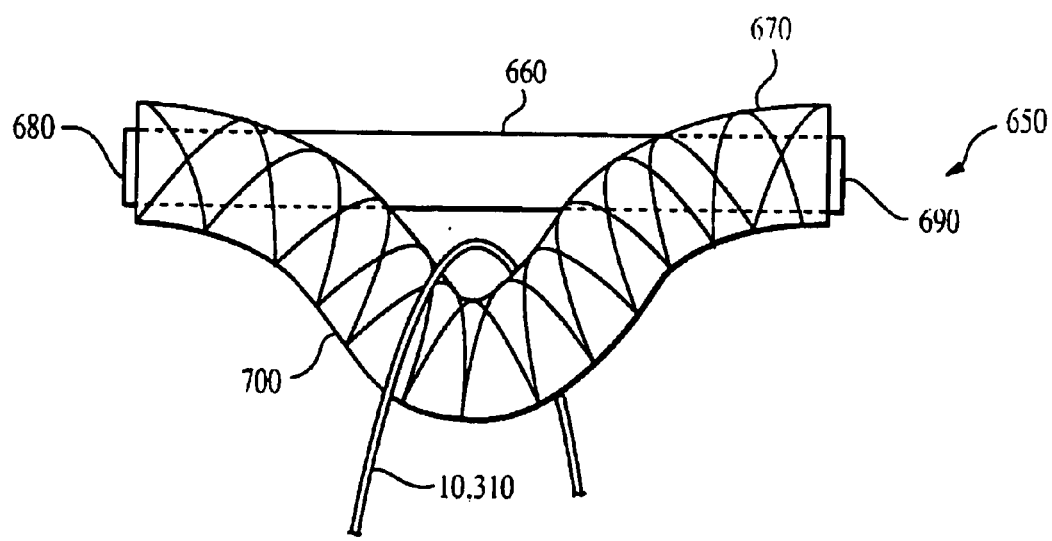

Referring to FIG. 25, an alternative embodiment of a fixation member 600, which can be used in any of the above embodiments, includes through bores 610, 620 with radiused corners 615 to reduce friction between suture 470 and fixation member 600. Referring to FIG. 26, another embodiment of a fixation member 650, which can be used in any of the above embodiments, includes a solid rod 660 with ends 680, 690, and a braided suture 670 attached to ends 680, 690. Suture 670 forms a loop 700 for receiving suture 10 or suture 310. Loop 700 lines up with suture 10, 310 to act as a pulley and reducing friction between the suture and fixation member.

The fixation members, securement elements, and suture of the above embodiments can be formed of a biodegradable material.

Other embodiments are within the scope of the following claims.

What is claimed is:

1. A flexible member holder, comprising:
   a tube,
   a shaft extending from the tube,
   a first tine at an end region of the shaft defining a first region for receiving a first portion of a loop of a flexible member,
   a second tine at the end region of the shaft defining a second region for receiving a second portion of the loop of the flexible member; and
   a tissue penetration device slidably received within the tube and configured to extend between the first and second regions.

2. The holder of claim 1 wherein the shaft extends distally from the tube.

3. The holder of claim 1 wherein each of the first and second regions comprises a groove.

4. The holder of claim 1 further comprising a fixation member to which the flexible member is attached.

5. The holder of claim 4 wherein the tissue penetration device is configured to receive the fixation member.

6. The holder of claim 4 wherein the fixation member includes a cylindrical region received within the tissue penetration device.

7. The holder of claim 4 wherein the fixation member includes a fin that extends through a slot of the tissue penetrating device.

8. The holder of claim 4 wherein the fixation member includes holes for receiving the flexible member.

9. The holder of claim 1 wherein the tissue penetrating device includes a slot.

10. The holder of claim 1 wherein the tube defines a lumen through which the tissue penetration device is slidable received.

11. The holder of claim 1 wherein the tissue penetration device includes a needle.

12. The holder of claim 1 wherein the tissue penetrating device includes a beveled tip.

13. The holder of claim 1 further comprising a handle for advancing the tissue penetration device relative to the shaft.

14. The holder of claim 1 wherein one or more of the tines is oriented along an axis that is different from a longitudinal axis of the tissue penetration device.

15. The holder of claim 1 wherein one or more of the first and second portions of the flexible member loop is oriented along an axis that is different from a longitudinal axis of the tissue penetration device.

16. A flexible member holder, comprising:
    a tube,
    a shaft extending from the tube and having:
      a first region for receiving a first portion of a loop of a flexible member,
      a second region for receiving a second portion of the loop of the flexible member; and
    a tissue penetration device slidably received within the tube and configured to extend between the first and second regions.

17. The holder of claim 16 wherein the shaft extends distally from the tube.

18. The holder of claim 16 wherein the tissue penetration device includes a needle.

19. The holder of claim 16 wherein the tissue penetration device includes a beveled tip.

20. The holder of claim 16 further comprising a handle for advancing the tissue penetration device relative to the shaft.

21. The holder of claim 16 wherein one or more of the first and second portions of the flexible member loop is oriented along an axis that is different from a longitudinal axis of the tissue penetration device.

22. A method of delivering an implant to body tissue, the method comprising:
    positioning a first portion of a loop of a flexible member at a first region of a shaft that extends from a tube,
    positioning a second portion of the loop of the flexible member at a second region of the shaft,
    sliding a tissue penetration device though the tube such that the tissue penetrating device extends between the first and second regions of the shaft.

23. The method of claim 22 wherein positioning the first portion includes positioning the first portion of the loop at a first tine at a first end region of the shaft, the first tine defining the first region.

24. The method of claim 22 wherein positioning the second portion includes positioning the second portion of the loop at a second tine at a second end region of the shaft, the second tine defining the second region.

25. The method of claim 22 further comprising advancing the tissue penetration device through the body tissue.

26. The method of claim 22 further comprising retracting the tissue penetration device from the body tissue.

27. The method of claim 25 further comprising advancing the tissue penetration device such that the tissue penetrating device exits the body tissue at a surface of the tissue after the tissue penetration device has been advanced through the body tissue.

28. The method of claim 22 further comprising advancing the tissue penetration device through a tear in the body tissue.

29. The method of claim 22 further comprising positioning a fixation member in the tissue penetration device.

30. The method of claim 29 further comprising attaching the flexible member to the fixation member.

31. The method of claim 30 wherein extending the tissue penetration device includes extending the fixation member.

32. The method of claim 31 further comprising advancing the tissue penetration device through the body tissue such that the fixation member is advanced through and exits the body tissue at a tissue surface.

33. The method of claim 32 further comprising retracting the tissue penetration device from the body tissue such that the fixation member remains at the tissue surface.

34. The holder of claim 16 wherein the shaft extends distally from the tube along a shaft axis and the first and second regions extend along a distal plane that is acute with the shaft axis.

35. The holder of claim 16 wherein the tube extends along a tube axis and the first and second regions extend along a distal plane that is 90 degrees or less from the tube axis.

36. A flexible member holder, comprising:
a tube,
a shaft extending from the tube and having:
a first region for receiving a first portion of a loop of a flexible member, and
a second region for receiving a second portion of the loop of the flexible member; and
a tissue penetrating elongate rigid member within the tube, the elongate rigid member being the sole elongate rigid member advanceable within the tube.

37. The holder of claim 36 wherein the tissue penetrating elongate rigid member is configured to extend between the first and second regions.

38. The holder of claim 36 further comprising a fixation member to which the flexible member is attached.

39. The holder of claim 38 wherein the tissue penetrating elongate rigid member is configured to receive the fixation member.

40. The holder of claim 38 wherein the fixation member includes a cylindrical region received within the tissue penetrating elongate rigid member.

41. The holder of claim 38 wherein the fixation member includes a fin that extends through a slot of the tissue penetrating elongate rigid member.

42. The holder of claim 38 wherein the fixation member includes holes for receiving the flexible member.

43. The holder of claim 36 wherein the tube defines a lumen through which the tissue penetration device is advanceable.

44. The holder of claim 36 wherein the tissue penetrating elongate rigid member includes a needle.

45. The holder of claim 36 wherein the tissue penetrating elongate rigid member includes a beveled tip.

46. The holder of claim 36 further comprising a handle for advancing the tissue penetrating elongate rigid member within the tube.

47. A flexible member holder, comprising:
a tube,
a shaft extending from the tube, and
a tissue penetrating elongate rigid member within the tube, the tissue penetrating elongate rigid member being the sole elongate rigid member advanceable within the tube,
wherein the shaft includes a distal portion with formations for receiving a flexible member and defining an opening for receiving the tissue penetrating elongate rigid member.

48. The holder of claim 47 wherein the tissue penetrating elongate rigid member is configured to extend through the opening.

49. The holder of claim 47 further comprising a fixation member to which the flexible member is attached.

50. The holder of claim 49 wherein the tissue penetrating elongate rigid member is configured to receive the fixation member.

51. The holder of claim 49 wherein the fixation member includes a cylindrical region received within the tissue penetrating elongate rigid member.

52. The holder of claim 49 wherein the fixation member includes a fin that extends through a slot of the tissue penetrating elongate rigid member.

53. The holder of claim 49 wherein the fixation member includes holes for receiving the flexible member.

54. The holder of claim 47 wherein the tube defines a lumen through which the tissue penetration device is advanceable.

55. The holder of claim 47 wherein the tissue penetrating elongate rigid member includes a needle.

56. The holder of claim 47 wherein the tissue penetrating elongate rigid member includes a beveled tip.

57. The holder of claim 47 further comprising a handle for advancing the tissue penetrating elongate rigid member within the tube.

58. A method of delivering an implant to body tissue, the method comprising:
positioning a first portion of a loop of a flexible member at a first region of a shaft that extends from a tube,
positioning a second portion of the loop of the flexible member at a second region of the shaft,
advancing an elongate rigid member through the tube, the elongate rigid member being the only elongate rigid member advanceable within the tube, and
piercing tissue with the elongate rigid member.

59. The method of claim 58 further comprising extending the elongate rigid member between the first and second regions of the shaft.

60. A method of delivering an implant to body tissue, the method comprising:
positioning a flexible member at formations of a distal portion of a shaft extending from a tube to define an opening,
advancing an elongate rigid member through the tube, the elongate rigid member being the only elongate rigid member advanceable within the tube, and
piercing tissue with the elongate rigid member.

61. The method of claim 60 further comprising extending the elongate rigid member through the opening.

* * * * *